(12) United States Patent
Maruhashi et al.

(10) Patent No.: US 7,930,156 B2
(45) Date of Patent: Apr. 19, 2011

(54) METHOD AND APPARATUS FOR SUPPORTING ANALYSIS OF GENE INTERACTION NETWORK, AND COMPUTER PRODUCT

(75) Inventors: Koji Maruhashi, Kawasaki (JP); Hiroshi Yamakawa, Kawasaki (JP); Yoshio Nakao, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 525 days.

(21) Appl. No.: 11/783,404

(22) Filed: Apr. 9, 2007

(65) Prior Publication Data

US 2007/0248977 A1    Oct. 25, 2007

(30) Foreign Application Priority Data

Apr. 21, 2006 (JP) ................................ 2006-118013

(51) Int. Cl.
*G06F 7/00* (2006.01)
(52) U.S. Cl. ................ 703/11; 702/19; 702/20; 703/12; 707/700
(58) Field of Classification Search ......................... None
See application file for complete search history.

(56) References Cited

U.S. PATENT DOCUMENTS

2004/0093331 A1 * 5/2004 Garner et al. ..................... 707/3
2004/0249620 A1 * 12/2004 Chandra et al. ................. 703/11

FOREIGN PATENT DOCUMENTS

JP    2003-044481    2/2003

OTHER PUBLICATIONS

Kyoto Encyclopedia of Genes of Genomes (KEGG), [online], searched on Feb. 27, 2006, the Internet <URL:http://www.genome.jp/kegg/pathway.html>.
Bio Carta, [online], searched on Feb. 27, 2006, the Internet: <URL:http://www.biocarta.com/>.

* cited by examiner

*Primary Examiner* — Mary K Zeman
(74) *Attorney, Agent, or Firm* — Staas & Halsey LLP

(57) ABSTRACT

Detailed information of each analysis subject partial network is displayed on a left pane of a screen. The detailed information includes the number of nodes, the number of edges, and accumulative coverage of the analysis subject partial network for each disease. Based on the detailed information, a user can designate the analysis subject partial network of a disease the user wishes to analyze. When the user has designated the disease, a network diagram indicating a partial network related to the designated disease is displayed on a right pane.

10 Claims, 21 Drawing Sheets

METHOD AND APPARATUS FOR SUPPORTING ANALYSIS OF GENE INTERACTION NETWORK, AND COMPUTER PRODUCT

CROSS-REFERENCE TO RELATED APPLICATIONS

This application is based upon and claims the benefit of priority from the prior Japanese Patent Application No. 2006-118013, filed on Apr. 21, 2006, the entire contents of which are incorporated herein by reference.

BACKGROUND OF THE INVENTION

1. Field of the Invention

The present invention relates a technology for supporting analysis of gene interaction network.

2. Description of the Related Art

In recent years, research for molecular mechanisms related to diseases is actively performed, based on differences in gene expression states between a patient and a healthy subject. Furthermore, research for effects of drugs on a living body at a molecular mechanism level is also often performed, based on differences in the gene expression states between when the drug is administered and when no drug is administered. In such researches, an assessment of relativity between a gene of interest and a disease or an estimation of effects of drugs on the gene of interest is widely performed through an analysis of gene interactions on individual genes in a gene cluster that is focused based on some clues.

In such analyses, it is preferable to appropriately select genes and the gene interactions to be analyzed depending on relationships with the disease. In other words, in general, a large number of genes of interest are acquired. The number of relevant gene interactions is enormous, and various interactions due different biological factors are present. Therefore, it is preferable to facilitate selection of an analysis subject (subject to be analyzed preferentially) by classification of the interactions according to the molecular mechanisms or by automatic selection of an interaction having high possibility to be related to the disease.

FIG. 21 is a schematic of gene interactions related to a gene cluster of interest, expressed in a network graph. A gene interaction network 2100 is formed by superimposing interaction networks that are respectively formed for a particular gene in each of the approximately 300 gene clusters of interest acquired by a gene expression analysis. A rectangular node indicates a gene. An edge indicates that a known interaction (interaction that has been reported in a document) is present between two genes corresponding to nodes on each end of the edge. As shown, a network that is a collection of interactions related to the genes of interest is often large and has a complex structure. Therefore, a technology for supporting analysis is demanded.

As a technology for supporting the analysis, databases in which the gene interaction networks are systematically accumulated while classifying the gene interactions according to types of diseases or in vivo molecular mechanism are known (for example, Kyoto Encyclopedia of Genes and Genomes (KEGG), [online], searched on Feb. 27, 2006, and BioCarta, [online], searched on Feb. 27, 2006. The interactions related the gene clusters of interest can be analyzed depending on disease or in vivo molecular mechanism, using of the databases.

Japanese Patent Laid-open Publication No. 2003-44481 discloses a technology for sorting genes that have high possibility to be related to a disease (disease-related gene). The sorting is performed in a gene interaction network as shown in FIG. 21.

According to the technology, identification of "research genes" is possible. To a gene cluster in which the differences in the gene expression states is observed when a certain drug is administered and when the drug is not administered, a gene clustering result, based on an appearance of a gene in a document, is presented. A relationship between the document in which the gene appears and the drug and the disease of interest is also presented. As a result, a gene that reacts to the drug and is expected to have relation with the disease of interest but has not been reported, is identified as the "research gene".

When a database, such as KEGG and BioCarta, is used, coverage of the database may be insufficient. The database is created manually, based on research findings acquired in a field of molecular biology. Therefore, gene interactions that are still being researched are not included. As a result, it cannot be expected that all gene interactions included in the gene interaction network 2100 are included in the database.

Furthermore, in the conventional technology disclosed in Japanese Patent Laid-open Publication No. 2003-44481, humans are required to interpret the gene interaction network 2100, while focusing on a specific drug and a specific disease, and judge relativity between individual genes and the disease. Therefore, it is difficult to apply the conventional technology as a support technology when there are plural diseases of interest.

In other words, presented information is required to be interpreted manually for each possible disease. Therefore, an efficient discovery and sorting of a disease-related gene is difficult. In general, one factor can increase a risk of plural diseases. Therefore, a technology for supporting analysis considering multiple diseases is demanded.

SUMMARY OF THE INVENTION

It is an object of the present invention to at least solve the above problems in the conventional technologies.

A computer-readable recording medium according to one aspect of the present invention stores therein a computer program for realizing a method of supporting analysis of gene interaction network. The computer program makes a computer execute setting a threshold for a relevance between a biological event and a gene interaction; detecting a gene interaction having a relevance equal to or higher than the threshold from among gene interactions forming the gene interaction network; and generating partial networks for respective biological events by arranging the gene interactions according to the biological events.

A method according to another aspect of the present invention is of supporting analysis of gene interaction network. The method includes setting a threshold for a relevance between a biological event and a gene interaction; detecting a gene interaction having a relevance equal to or higher than the threshold from among gene interactions forming the gene interaction network; and generating a partial network for each biological event by arranging the gene interactions according to the biological event.

An apparatus according to still another aspect of the present invention is for supporting analysis of gene interaction network. The apparatus includes a setting unit configured to set a threshold for relevance between a biological event and a gene interaction; a detecting unit configured detect a gene interaction having a relevance equal to or higher than the threshold from among gene interactions forming the gene interaction network; and a generating unit configured to generate a partial network for each biological event by arranging the gene interactions according to the biological event.

The other objects, features, and advantages of the present invention are specifically set forth in or will become apparent from the following detailed description of the invention when read in conjunction with the accompanying drawings.

DETAILED DESCRIPTION OF THE PREFERRED EMBODIMENTS

Exemplary embodiments according to the present invention will be explained in detail below with reference to the accompanying drawings.

Figure 1:
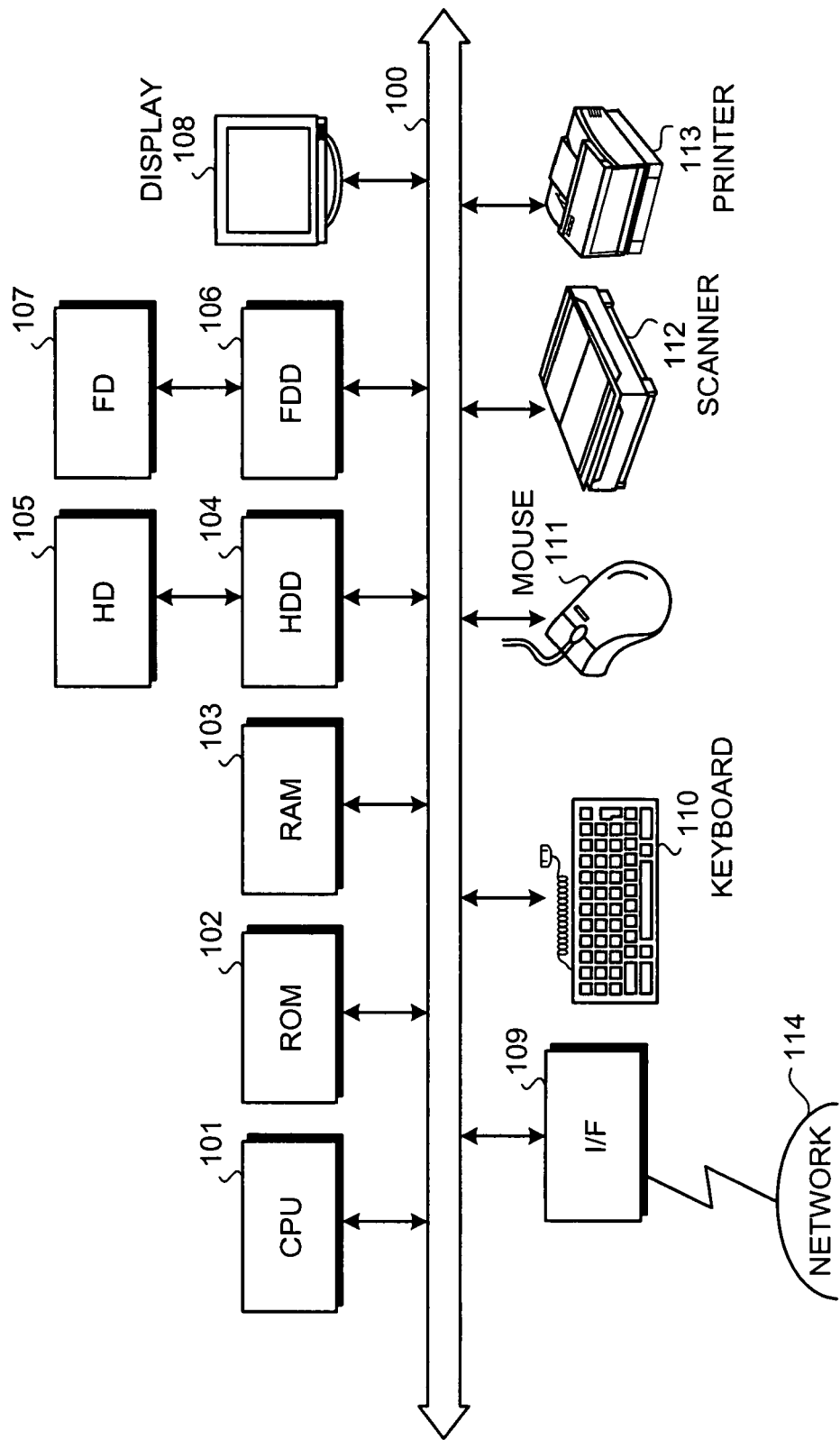
FIG. 1 is a schematic of an apparatus for supporting analysis of gene interaction network according to an embodiment of the present invention.

FIG. 1 is a schematic of an apparatus for supporting analysis of gene interaction network according to an embodiment of the present invention. The apparatus includes a central processing unit (CPU) 101, a read-only memory (ROM) 102, a random access memory (RAM) 103, a hard disk drive (HDD) 104, a hard disk (HD) 105, a flexible disk drive (FDD) 106, a flexible disk (FD) 107, a display 108, an interface (I/F) 109, a keyboard 110, a mouse 111, a scanner 112, and a printer 113. The FD 107 is an example of a removable recording medium. Each component is connected via a bus 100.

The CPU 101 controls the entire apparatus. The ROM 102 stores programs, such as a boot program. The RAM 103 is used as a work-area of the CPU 101. The HDD 104 controls reading and writing of data from and to the HD 105, under the control of the CPU 101. The HD 105 stores the data written under the control of the HDD 104.

The FDD 106 controls reading and writing of data from and to the FD 107, under the control of the CPU 101. The FD 107 stores the data written under the control of the FDD 106 and allows the apparatus to read the data stored in the FD 107.

Besides the FD 107, a compact-disc read-only memory (CD-ROM), a compact disc-recordable (CD-R), and a compact-disc rewritable (CD-RW), a magneto optical (MO) disk, a digital versatile disk (DVD), a memory card, and the like can be used as the removable recording medium. The display 108 displays data, such as documents, images, and function information, in addition to a cursor, icons, and toolboxes. The display 108 may be, for example, a cathode ray tube (CRT), a thin film transistor (TFT) liquid-crystal display, or a plasma display.

The I/F 109 is connected to a network 114, such as the internet, via a communication circuit. The I/F 109 is connected to other devices via the network 114. The I/F 109 controls an interface between the apparatus and the network 114 and controls input and output of data from and to an external device. The I/F 109 can be, for example, a modem or a LAN adapter.

The keyboard 110 includes keys for inputting characters, numbers, various instructions, and the like. The keyboard 110 performs data input. The keyboard 110 can also be a touch-panel input pad, a numeric keypad, or the like. The mouse 111 moves the cursor, selects a range, moves windows, changes window size, and the like. The mouse 111 can also be a track ball, a joystick, or the like, that similarly functions as a pointing device.

The scanner 112 optically reads an image and loads image data into the apparatus. The scanner 112 can have a function of optical character recognition (OCR). The printer 113 prints the image data and document data. The printer 113 can be, for example, a laser printer or an ink-jet printer.

Figure 2:
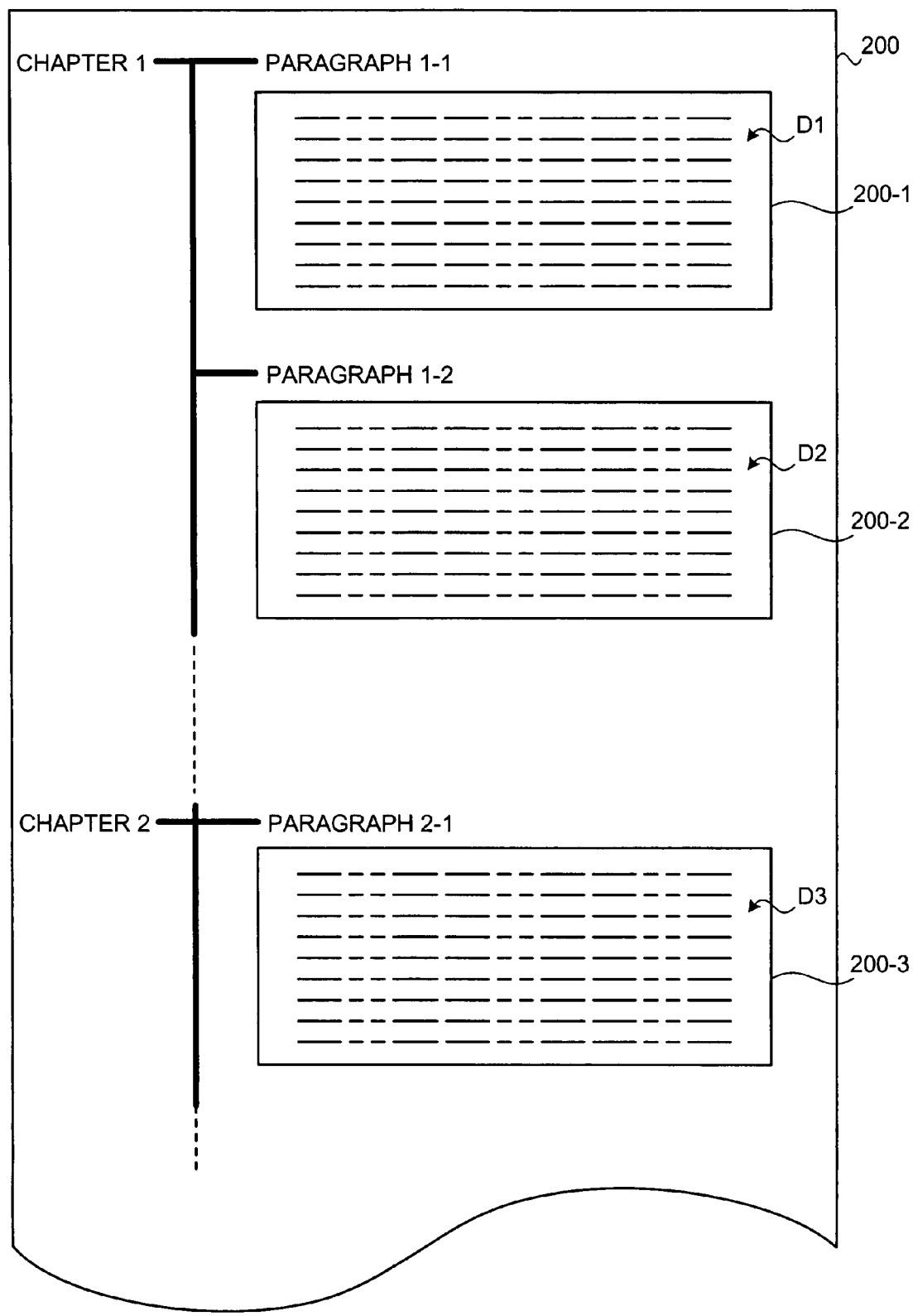
FIG. 2 is a schematic for illustrating a disease annotation according to the embodiment.

FIG. 2 is a schematic for illustrating a disease annotation according to the embodiment. A disease annotation 200 is a body of knowledge document. In the disease annotation 200, a biological event (including, for example, physiological actions of a substance, biological responses, clinical symptoms, and the like that are related to a disease) is systematically described in a natural language. Explanations related to the disease are written, for example, in chapters and in paragraphs.

An explanation is provided for each disease. For example, "disease D1" is explained in an explanation 200-1 in "paragraph 1-1" of "chapter 1". "disease D2" is explained in an explanation 200-2 in "paragraph 1-2" of "chapter 1". "disease D3" is explained in an explanation 200-3 in "paragraph 2-1" of "chapter 2".

The disease annotation 200 is, for example, an electronic document that has been converted into text. The disease annotation 200 can be input from the I/F 109, shown in FIG. 1, or can be recorded on the recording medium, such as the ROM 102, the RAM 103, and the HD 105.

An electronic document, Online Mendelian Inheritance in Man (OMIM), and the like can be used as the disease annotation 200.

OMIM is an electronic version of "Mendelian Inheritance in Man," a collection of information on phenotypes, gene loci, and the like of human genetic disorders, authored by Dr. Victor A. McKusick.

Figure 3:
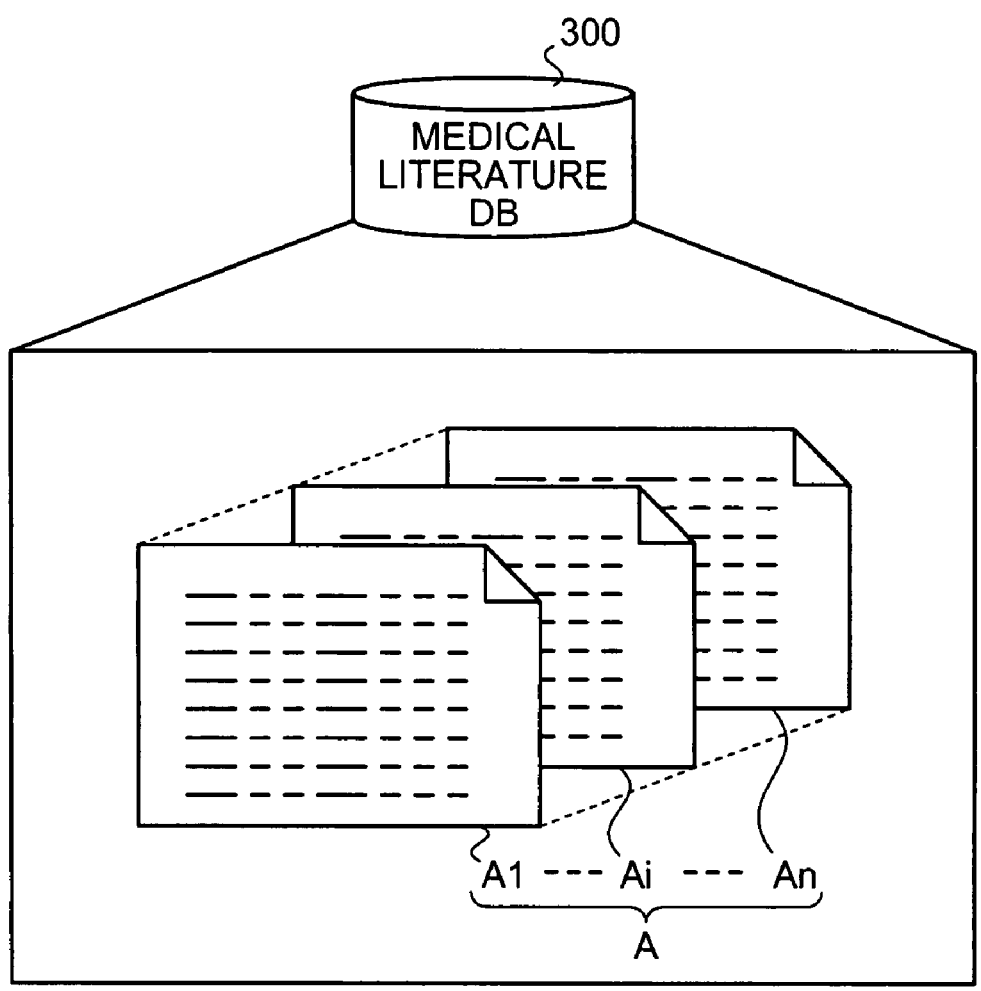
FIG. 3 is a schematic for illustrating a medical literature database (DB) according to the embodiment.

FIG. 3 is a schematic for illustrating contents stored in a medical literature DB according to the embodiment. A medical literature DB 300 stores electronic literature A (Ai: i=1 to n) containing biological and medical research findings related to interactions between genes, and the like.

The electronic literature A is electronic data, such as abstracts stored in Medical Literature Analysis and Retrieval System On-Line (MEDLINE) and in databases similar to MEDLINE.

MEDLINE is a secondary source database of indexes and abstracts of medical literature, provided by the United States National Library of Medicine (NLM). PubMed is a widely used literature retrieval tool for MEDLINE, provided by the National Center for Biotechnology Information (NCBI). The electronic literature A is converted into text and stored in a database.

In the embodiment, in addition to the contents (text) of an electronic literature Ai, a correspondence between the electronic literature Ai and a gene interaction reported in the electronic literature Ai are used. If the correspondence is included within bibliographic information or the like in the electronic literature Ai, the included correspondence can be used.

In the MEDLINE database, correspondences between gene interactions and MEDLINE literature are included in "Interactions" information provided in an Entrez Gene database, disclosed by the NLM. Therefore, the described correspondences can be used. Hereafter, the gene interaction corresponding to any one of electronic literature, A1 to An, is referred to as a gene interaction I (Ij: j=1, 2, etc.).

Figure 4:
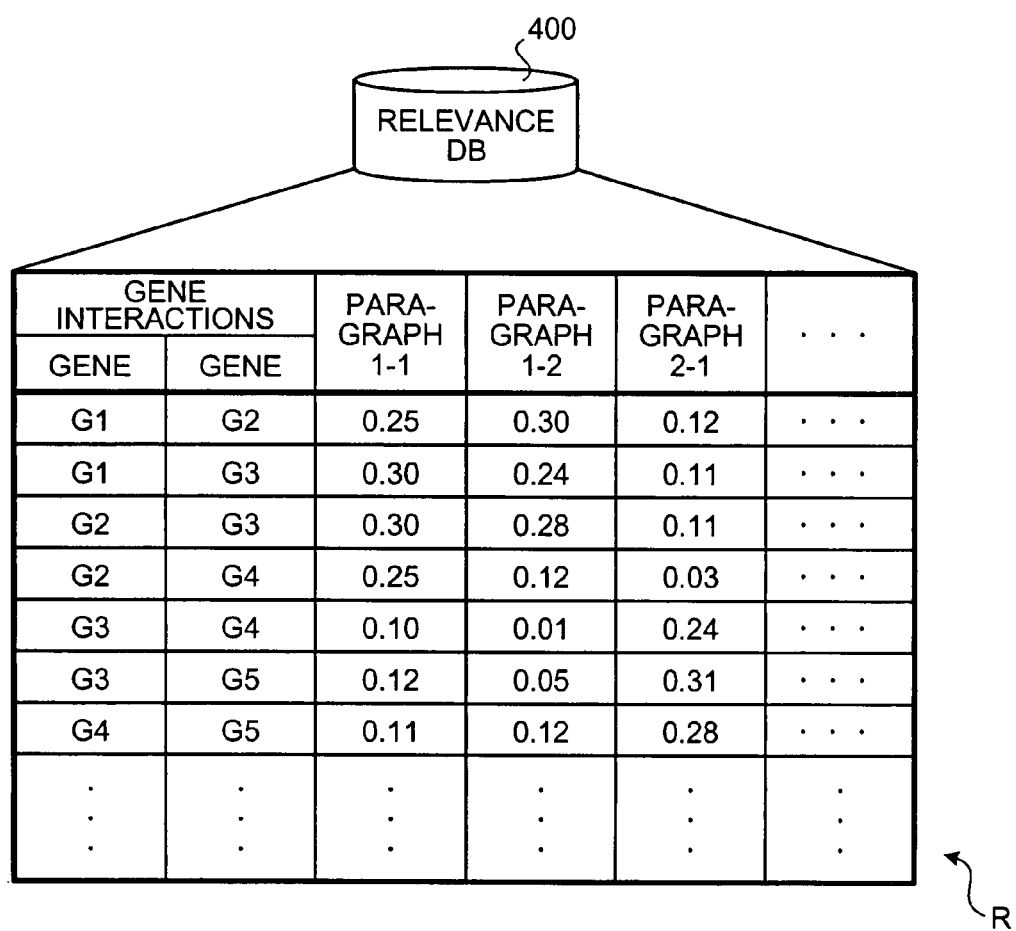
FIG. 4 is a schematic for illustrating the medical literature database (DB) according to the embodiment.

FIG. 4 is a schematic for illustrating contents stored in a relevance DB according to the embodiment. A relevance DB 400 stores relevance.

A relevance is a value specified by a paragraph number of the disease annotation 200 that specifies each disease and two genes that are bases of the gene interaction. For example, the relevance is calculated by the disease annotation 200 in FIG. 2 and the electronic literature A within the medical literature DB 300 in FIG. 3. If the relevance is R, a relevance R is $0 \leq R \leq 1$. If a value of the relevance R is large, a connection between the disease and the gene interaction is considered strong.

Figure 5:
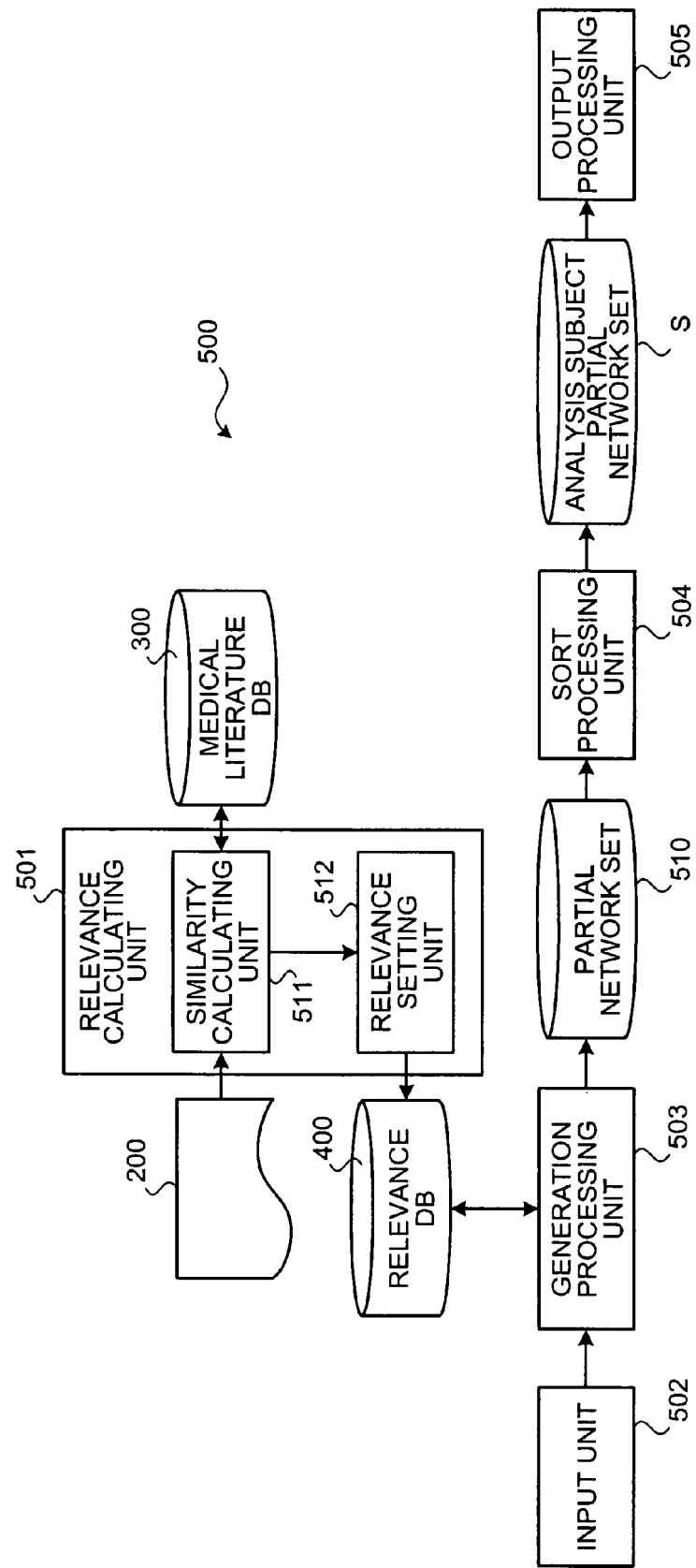
FIG. 5 is a block diagram of the apparatus according to the embodiment.

FIG. 5 is a block diagram of the apparatus according to the embodiment. An apparatus for supporting analysis of gene interaction network 500 includes the disease annotation 200, the medical literature DB 300, the relevance DB 400, a relevance calculating unit 501, an input unit 502, a generation processing unit 503, a sort processing unit 504, and an output processing unit 505.

The relevance calculating unit 501 calculates the relevance R stored in the relevance DB 400. Specifically, the relevance calculating unit 501 includes a similarity calculating unit 511 and a relevance setting unit 512. The similarity calculating unit 511 calculates similarity between the disease annotation 200 and each electronic document Ai within the medical literature DB 300.

Figure 6:
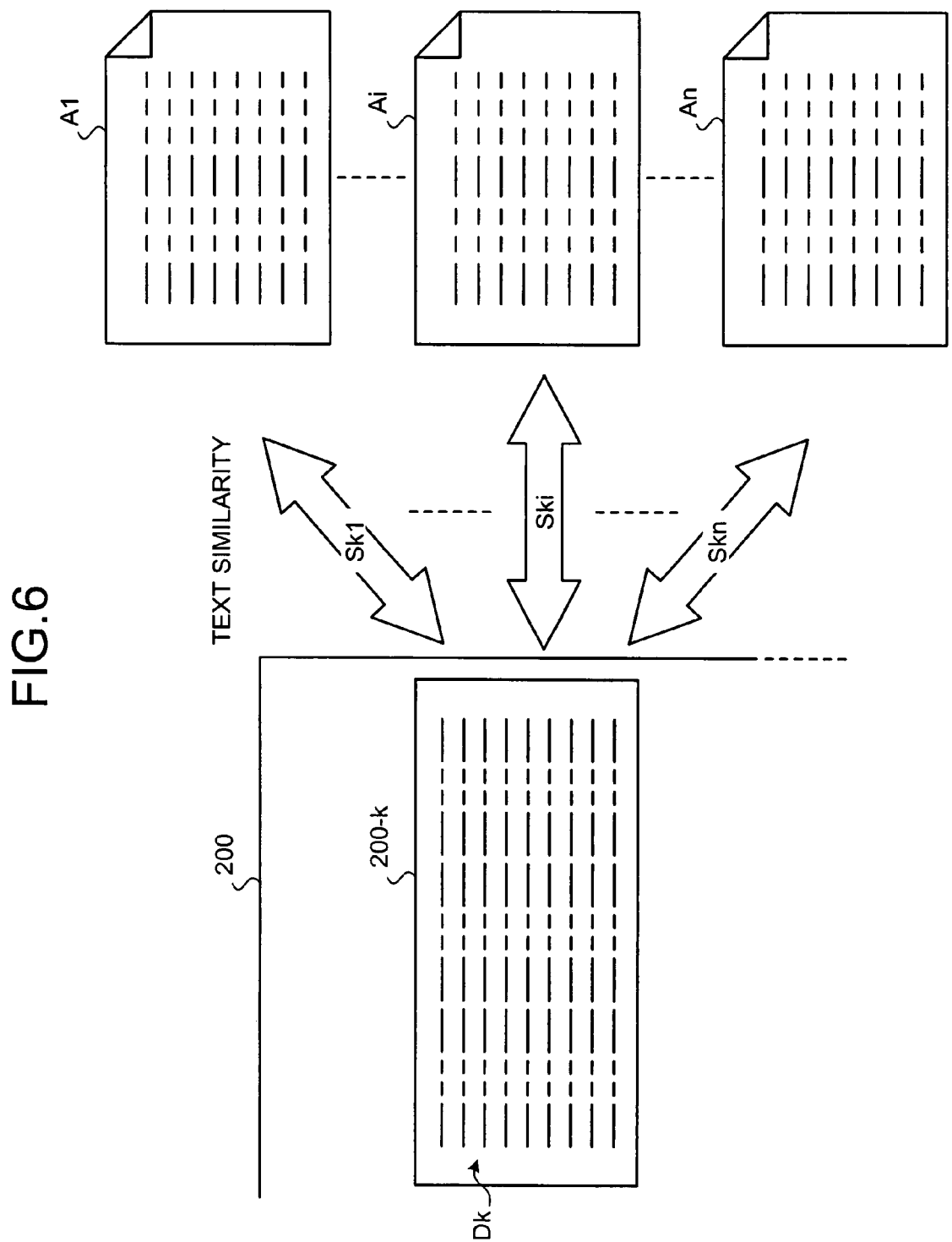
FIG. 6 is a schematic for illustrating a similarity calculation performed by a similarity calculating unit.

FIG. 6 is a schematic for illustrating the similarity calculation performed by the similarity calculating unit 511. Text similarity between an explanation 200-$k$ (k=1, 2, etc.) and the electronic literature Ai is calculated by a term frequency-inverse document frequency (TFIDF) method. The text similarity is calculated using text data in the explanation 200-$k$ of a disease Dk in the disease annotation 200 and text data in the electronic document Ai.

Specifically, an appearance frequency of a keyword candidate appearing in the explanation 200-$k$ and the appearance frequency of the keyword candidate appearing in the electronic document Ai are obtained by term frequency (TF). A logarithm of an inverse number of a frequency by which the keyword candidate appears in a document (explanation 200-$k$ and electronic document Ai) is obtained by inverse document frequency (IDF) (a logarithm of the inverse document). A TFIDF vector obtained by a product of the TF and the IDF is calculated for each document (explanation 200-$k$ and electronic document Ai).

A cosine value (a dot product value of a vector normalized to size 1) of the TFIDF vector of the explanation 200-$k$ and the TFIDF vector of the electronic literature Ai is a text similarity Ski ($0 \leq Ski \leq 1$) of the explanation 200-$k$ and the electronic literature Ai. The larger a value of the text similarity Ski is, the more similar the explanation 200-$k$ and the electronic literature Ai are.

The relevance setting unit 512 sets the relevance R between a gene interaction Ij and the disease Dk, using the disease annotation 200 and the electronic literature A. Specifically, the relevance setting unit 512 sets a relevance Rjk between the gene interaction Ij and the disease Dk, based on the text similarity Ski calculated for each electronic literature Ai by the similarity calculating unit 511. More specifically, the relevance setting unit 512 sets the relevance Rjk, based on a set Σjk of an m (m≦n) number of text similarities corresponding to the gene interaction Ij. The set Σjk is a set of text similarities. Elements of the set Σjk are the text similarities among Sk1 to Skn that correspond to the gene interaction Ij.

For example, the relevance Rjk can be a highest text similarity among the m number of text similarities Σjk. Alternatively, the relevance Rjk can be a lowest text similarity among the m number of text similarities Σjk. The relevance Rjk can also be a median value of the m number of text similarities Σjk or an average value of the m number of text similarities Σjk. The relevance R in FIG. 4 is a set of relevance Rjk obtained for each combination of the gene interaction Ij and the explanation 200-$k$ in this way.

As described above, the relevance DB 400 can be created through calculations by the relevance calculating unit 501. However, the relevance DB 400 that is provided with the relevance Rjk in advance can also be used in the apparatus 500.

Figure 21:
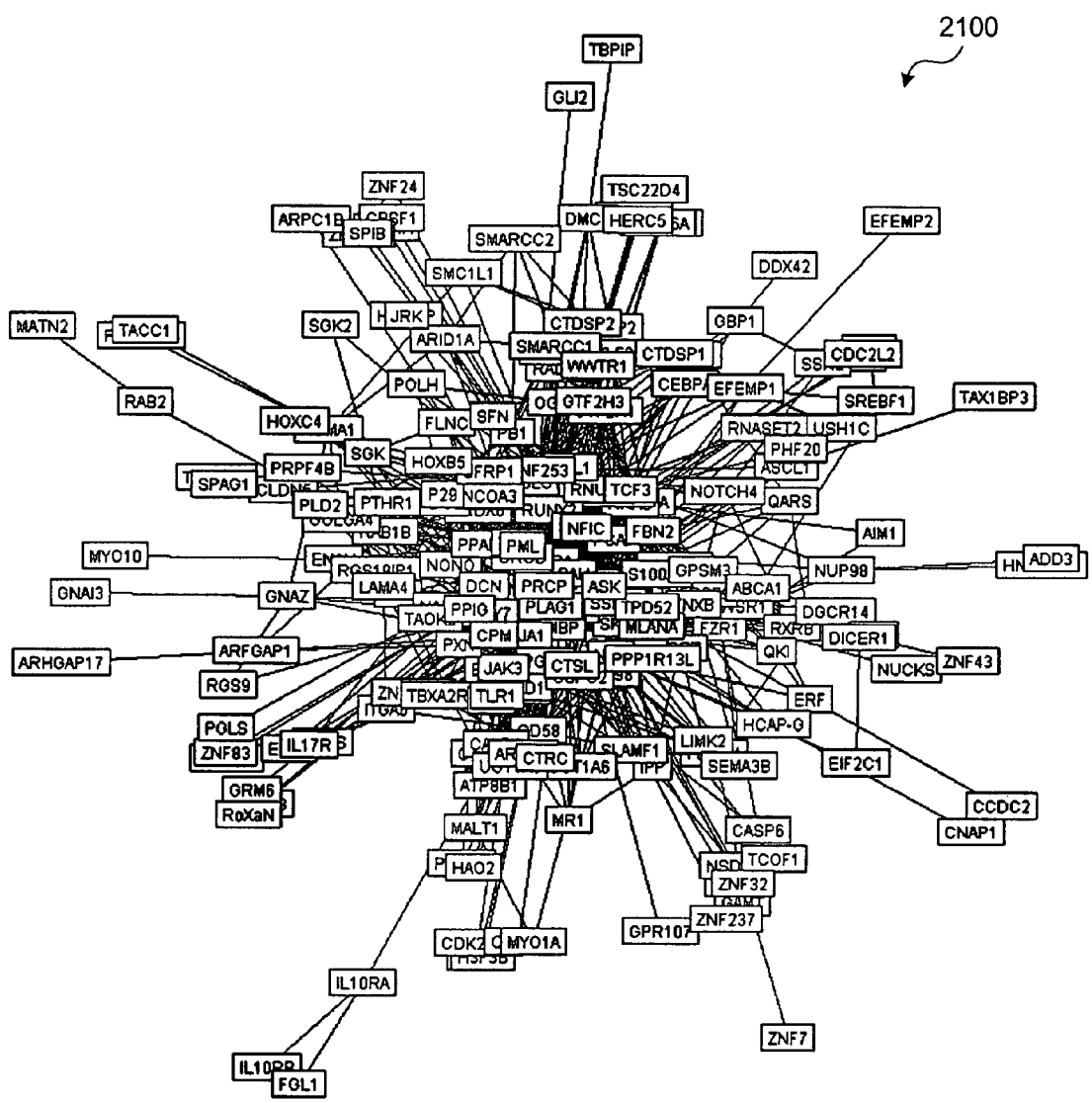
FIG. 21 is a schematic of a gene interaction network.

The input unit 502 receives an input of the gene interaction network 2100, such as that shown in FIG. 21. Specifically, the gene interaction network 2100 is input from the ROM 102, the RAM 103, the HD 105, the I/F 109, the scanner 112, or the like, through operation of the keyboard 110 or the mouse 111, shown in FIG. 1.

The generation processing unit 503 generates a plurality of partial network sets 510 for each biological event, based on the relevance R between the biological event and the gene interaction. The partial network sets 510 are portions of the gene interaction network 2100. Details of the generation processing unit 503 will be described hereafter.

The sort processing unit 504 selects a partial network set to be an analysis subject (hereinafter, "analysis subject partial network set S") from among the partial network sets 510. The analysis subject partial network set S is selected based on a number of edges in the partial network set 510 generated for each biological event by the generation processing unit 503. Details of the sort processing unit 504 will be described hereafter. The output processing unit 505 outputs the analysis subject partial network set S. Specifically, the output processing unit 505 displays the analysis subject partial network set S on a display screen of the display 108 or prints out the analysis subject partial network set S from the printer 113.

Functions of the relevance calculating unit 501, the input unit 502, the generation processing unit 503, the sort processing unit 504, and the output processing unit 505 are actualized, for example, by execution of a program recorded on the recording medium, such as the ROM 102, the RAM 103, and the HD 105. Alternatively, the functions are actualized by the I/F 109.

Figure 7:
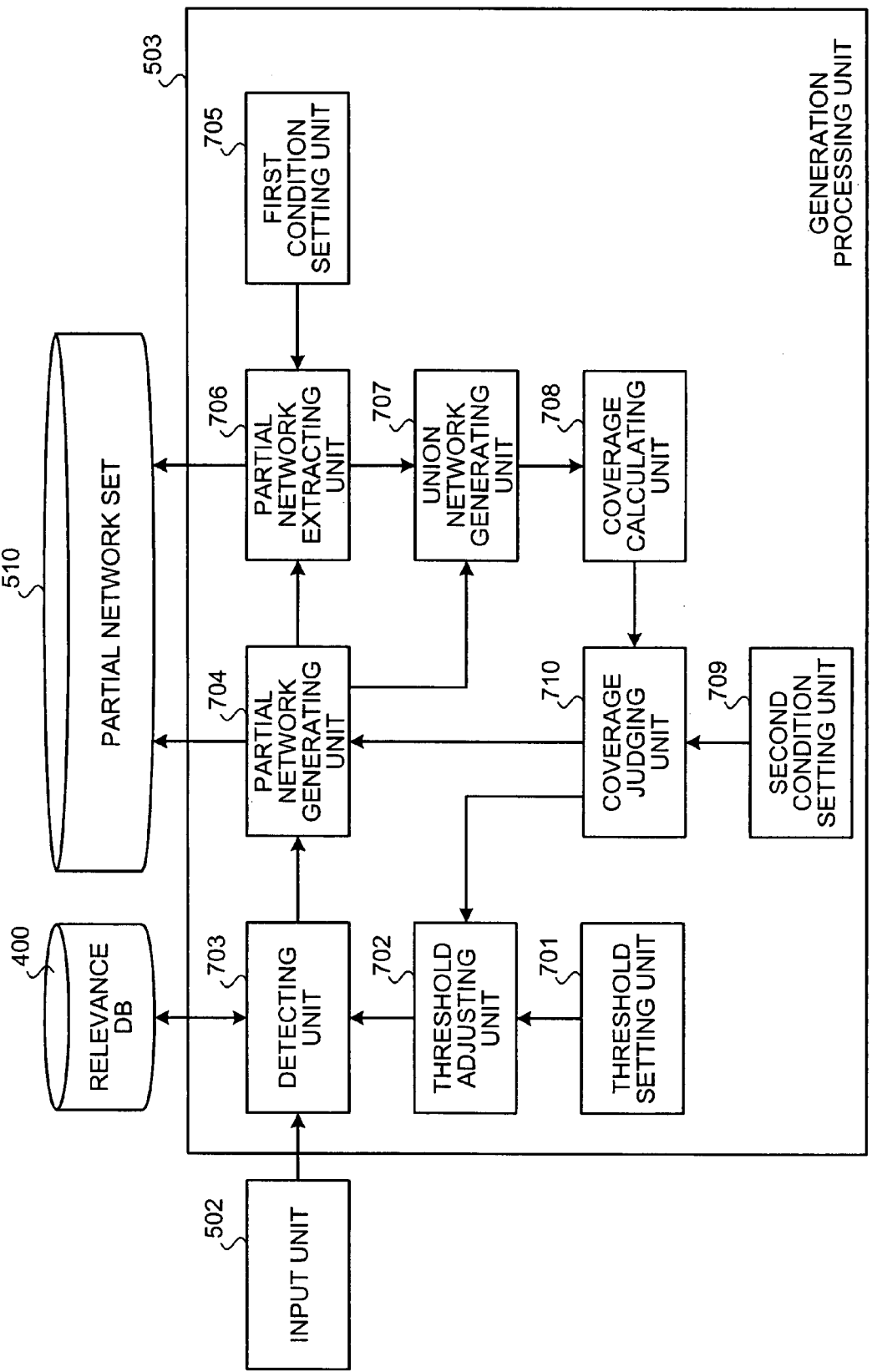
FIG. 7 is a block diagram of a generation processing unit.

FIG. 7 is a block diagram of the generation processing unit 503. The generation processing unit 503 includes a threshold setting unit 701, a threshold adjusting unit 702, a detecting unit 703, a partial network generating unit 704, a first condition setting unit 705, a partial network extracting unit 706, a union network generating unit 707, a coverage calculating unit 708, a second condition setting unit 709, and a coverage judging unit 710.

The threshold setting unit 701 sets a threshold T related to the relevance between the biological event and the gene interaction I. The threshold T is used to detect the gene interaction I having a relevance that is equal to or higher than the threshold T. The threshold T is arbitrarily set by a user. The threshold T can be adjusted by lowering in stages. Therefore, an initial value is preferably set to a maximum value Tmax of the relevance R.

The threshold adjusting unit 702 adjusts the threshold T so that the threshold T is lowered in stages. An amount ΔT by which the threshold T is lowered can be arbitrarily set by the user. The amount ΔT can be set freely. For example, ΔT=0.01. Timing for adjusting the threshold T will be described hereafter.

The detecting unit 703 detects a gene interaction Ijk among gene interactions I that form a gene interaction network. The gene interaction Ijk has the relevance R that is equal to or higher than the threshold T. Specifically, the detecting unit 703 detects the gene interaction Ij from the relevance DB 400. The gene interaction Ij, among the gene interactions I, has the relevance Rjk with any one of the diseases Dk that is equal to or higher than the threshold T.

For example, as shown in FIG. 4, if the threshold T=0.30, the relevance R that is equal to or higher than 0.30 is in two rows (relevance R=0.30) in a column of the paragraph 1-1 (disease D1) and one row (relevance R=0.31) in a column of the paragraph 2-1 (disease D3). Three combinations, (gene G1, gene G3), (gene G2, gene G3), and (gene G3, gene G5), are detected as the gene interactions corresponding to the relevance above.

The gene interaction Ij, among the gene interactions I, has the relevance Rjk with any one of the diseases Dk that is equal to or higher than the threshold T. If the gene interaction Ij is not detected from the relevance DB 400, the threshold adjusting unit 702 reduces the threshold T by the predetermined amount ΔT. Therefore, the threshold T that has been lowered by the predetermined amount ΔT becomes a reference for detection by the detecting unit 703. In this way, at least one gene interaction having the relevance with any one of the diseases that is equal to or higher than the threshold T, can be found through adjusting the threshold T in stages.

Figure 8:
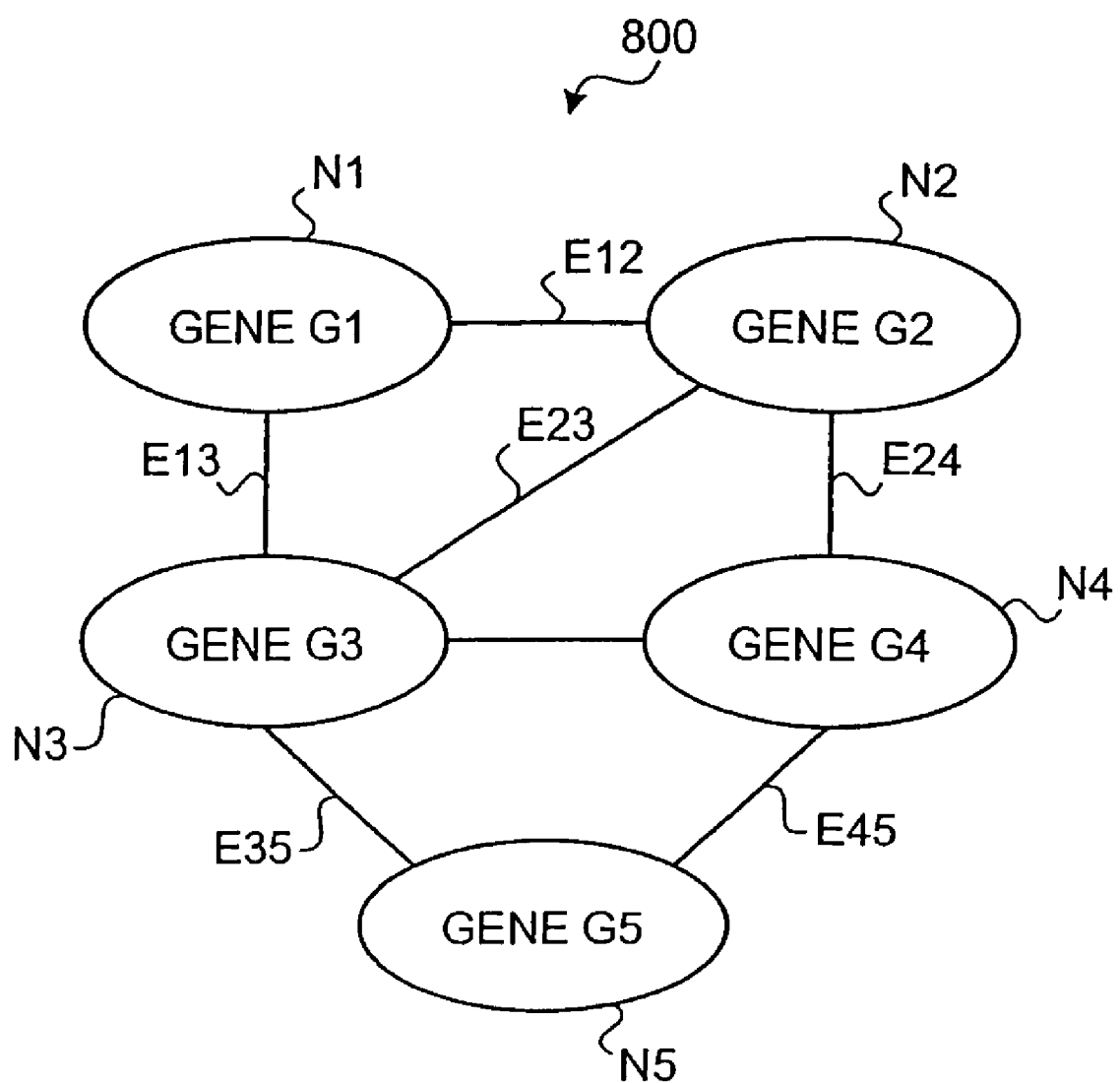
FIG. 8 is a schematic of a gene interaction network input by an input unit.
Figure 9:
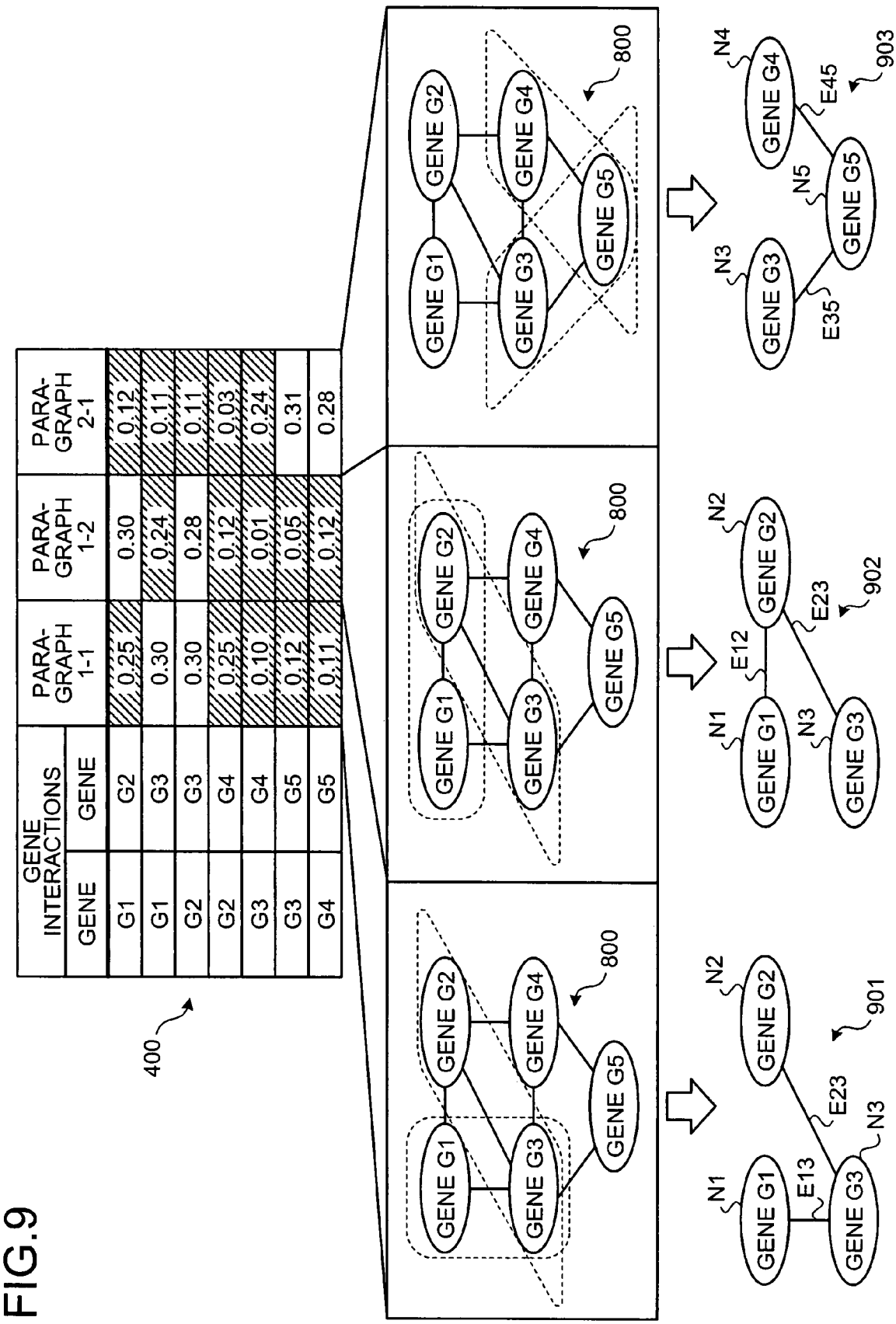
FIG. 9 is a schematic for illustrating a generation process by a partial network generating unit.

The partial network generating unit 704 generates the partial network set 510 for each disease Dk, based on the relevance Rjk between the disease Dk and the gene interaction Ij. The gene interaction Ij is detected by the detecting unit 703. FIG. 8 is a schematic of the gene interaction network input by the input unit 502. FIG. 9 is a schematic for illustrating a generation process by the partial network generating unit 704.

As shown in FIG. 8, a gene interaction network 800 includes nodes Nx (x=1 to 5) and edges Exy (y=1 to 5, y≠x). A node Nx specifies a gene Gx. An edge Exy connects the node Nx and a node Ny. In actuality, the gene interaction network 800 is complex. The gene interaction network 800 has large numbers of nodes and edges, as does the gene interaction network 2100 shown in FIG. 21. However, in the example, the gene interaction network 800 is simplified and has five nodes and seven edges.

An upper section shown in FIG. 9 illustrates the contents stored in the relevance DB 400. A middle section illustrates results of the detection by the detecting unit 703. A lower section illustrates generated partial networks 901 to 903. When the threshold T of the relevance R is, for example, T=0.27, the relevance Rjk that is equal to or higher than the threshold T is un-shaded relevance Rjk shown in the upper section.

In the middle section, the gene interaction network 800 on the left-hand side shows detection results of the gene interactions related to the disease in the paragraph 1-1. The nodes and edges that are surrounded by dotted lines are the detected gene interactions. The gene interaction network 800 in the center shows the detection results of the gene interactions related to the disease in paragraph 1-2. The nodes and edges that are surrounded by dotted lines are the detected gene interactions. The gene interaction network 800 on the right-hand side shows the detection results of the gene interactions related to the disease in paragraph 2-1. The nodes and edges that are surrounded by dotted lines are the detected gene interactions.

As shown in the lower section, the nodes and edges forming the gene interactions that are surrounded by the dotted lines in the middle section are obtained as partial networks 901 to 903, for each paragraph (disease).

The first condition setting unit 705 shown in FIG. 7 sets a first condition to limit a size or complexity of a generated partial network. The condition to limit the size of the partial network limits the size of the partial network to a predetermined range. The predetermined range is, for example, a range of a number of nodes indicating the genes to be included in each partial network, a range of a number of types of nodes to be included in the network, or the like.

The condition to limit the complexity of the partial network limits the complexity of the partial network to a predetermined level. The predetermined level is, for example, a range of a number of edges indicating the gene interactions to be included in each partial network, a range of a number of types of edges to be included in the network (or a ratio of the number of types of edges indicating the gene interactions to the number of types of nodes indicating the genes), or the like.

The partial network extracting unit 706 extracts the partial network that satisfies the first condition from among the partial network set 510. For example, if the first condition is "less than three nodes", the partial networks within the partial network set 510 that have less than three nodes are extracted.

According to the first condition setting unit 705 and the partial network extracting unit 706, the size and the complexity of the partial network to be a candidate for the analysis subject can be controlled. Therefore, a small-scale partial network having a simple structure can be analyzed.

The union network generating unit 707 generates a union network by compiling the partial networks. The partial network that becomes a generator of the union network can be the partial networks generated by the partial network generating unit 704 and any of the partial networks extracted by the partial network extracting unit 706. The union network includes all partial networks that become the generator. The nodes and edges that are not included in any of the partial networks that become the generator are not included.

Figure 10:
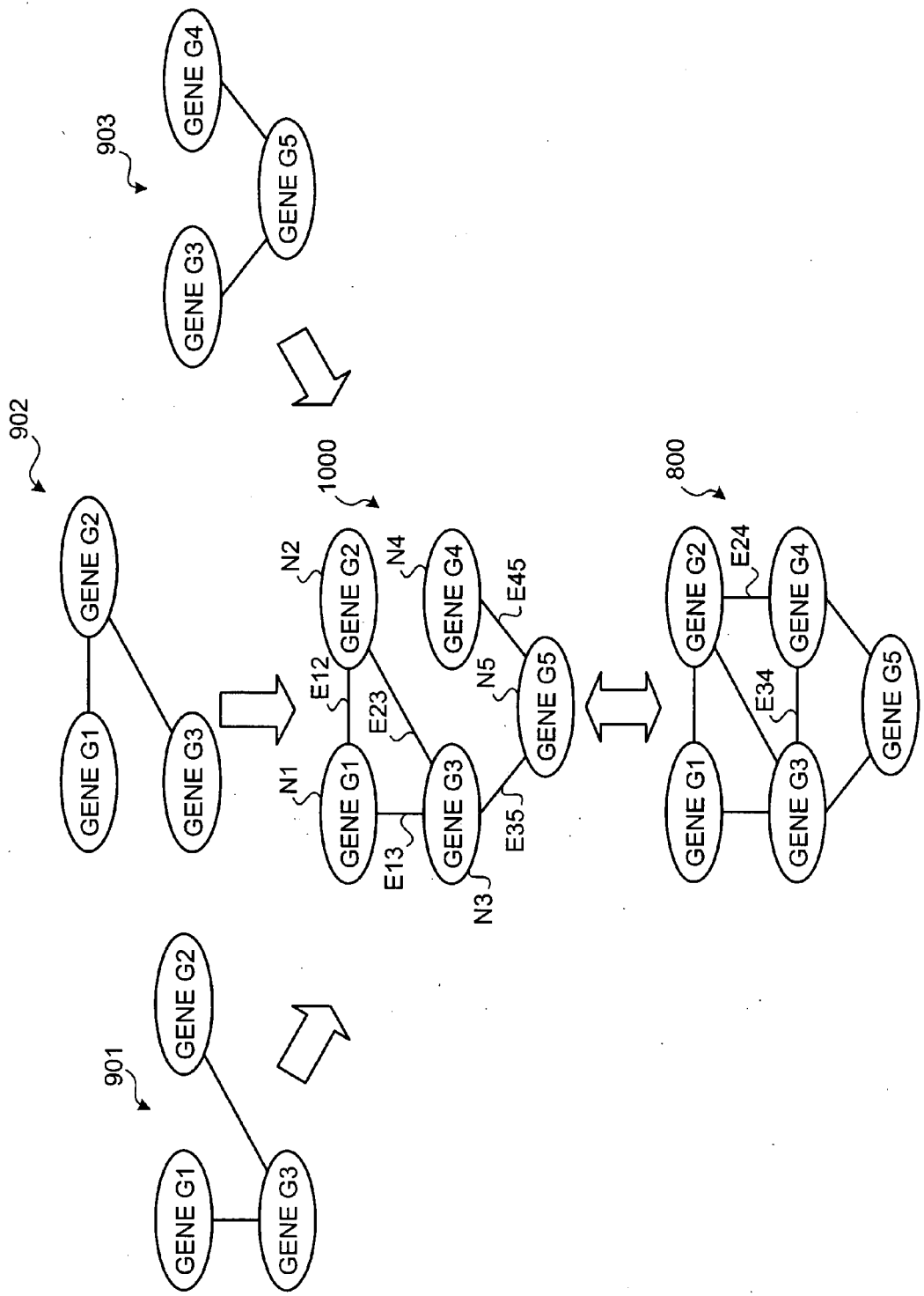
FIG. 10 is a schematic for illustrating generation of a union network.

FIG. 10 is a schematic for illustrating generation of a union network. When generating a union, a union network 1000 includes the nodes Nx and the edges Exy included in each partial network 901 to 903. The union network 1000 includes nodes N1 to N5, and edges E12, E13, E23, E35, and E45.

The coverage calculating unit 708 shown in FIG. 7 calculates a coverage that indicates a degree by which the union network is included in the gene interaction network. Specifically, the coverage can be expressed by a following Equation 1 or Equation 2.

$$C=Me1/Me0 \quad (1)$$

$$C=Mn1/Mn0 \quad (2)$$

C is the coverage. Me1 is the number of edges in the union network. Me0 is the number of edges in the gene interaction network. Mn1 is the number of nodes in the union network. Mn0 is the number of nodes in the gene interaction network. The user sets whether to use the number of nodes or the number of edges. However, under the premise that a purpose of an analysis is to infer a role of the gene in the biological event and the like, the role of the gene may be dependent on the gene that is an interacting partner. Therefore, the coverage (1) that is calculated by the number of edges is preferable. Calculating the coverage by the number of edges is equivalent to calculating the coverage per gene interaction.

In the example shown in FIG. 10, when the coverage is calculated by the number of edges, the union network 1000 has five edges and the gene interaction network 800 has seven edges. Therefore, the coverage C is 5/7.

The second condition setting unit 709 sets a condition to limit coverage of the analysis subject. The condition to limit the coverage of the analysis subject limits the number of edges indicating the gene interactions that should collectively be included in a plurality of partial networks. For example, a specified coverage Ct is set. The specified coverage Ct is a threshold of the coverage described above. When enhancing overall coverage of the union network, a value of the specified coverage Ct is increased.

The coverage judging unit 710 judges whether the coverage C satisfies the second condition. For example, the coverage judging unit 710 judges whether the calculated coverage C is equal to or higher than the specified coverage Ct. If the coverage C is equal to or higher than the specified coverage Ct, the overall coverage of the partial network set 510 increases. The partial network set 510 becomes a calculation source of the coverage C.

Therefore, a user request for enhanced coverage is met. In this case, the partial network generating unit 704 outputs the partial network set 510 that become the calculation source of the coverage C. On the other hand, if the coverage C is lower than the specified coverage Ct, the overall coverage of the partial networks that become the calculation source of the coverage C is reduced. Therefore, the user request is not met.

In this case, the threshold adjusting unit 702 lowers the threshold T by the predetermined amount ΔT. When the threshold is lowered by ΔT, the detecting unit 703 detects the gene interaction Ij from the relevance DB 400. The gene interaction Ij, among the gene interactions I, has the relevance Rjk with any one of the diseases Dk that is equal to or higher than the predetermined threshold T after being lowered by ΔT. As a result, the number of detected gene interactions is increased and the partial networks generated by the partial network generating unit 704 become larger. Therefore, the union network also becomes larger. The currently calculated coverage C is a larger value than a previously calculated coverage C.

The number of gene interactions collectively included in the output partial networks can be controlled by adjusting the threshold T in stages. Therefore, for example, if all output partial networks are analyzed, a following user request can be met. The user requests for a guarantee that a majority of the interactions included in an original gene interaction network can be comprehensively analyzed.

In this way, when the gene interaction networks 800 and 2100 are divided into each biological event (disease), the generation processing unit 503 can provide appropriately sized partial networks. In addition, the generation processing unit 503 can enhance the coverage of the partial networks of the gene interaction networks 800 and 2100, to an utmost extent.

If the coverage is high, the number of nodes and the number of edges in the union network 1000 increase and the gene interactions in the union network 1000 becomes complex. However, the gene interaction network 800 is generated for each biological event. Therefore, the partial networks 901 to 903 that are appropriately sized to a minimum size required for analysis can be obtained.

Figure 11:
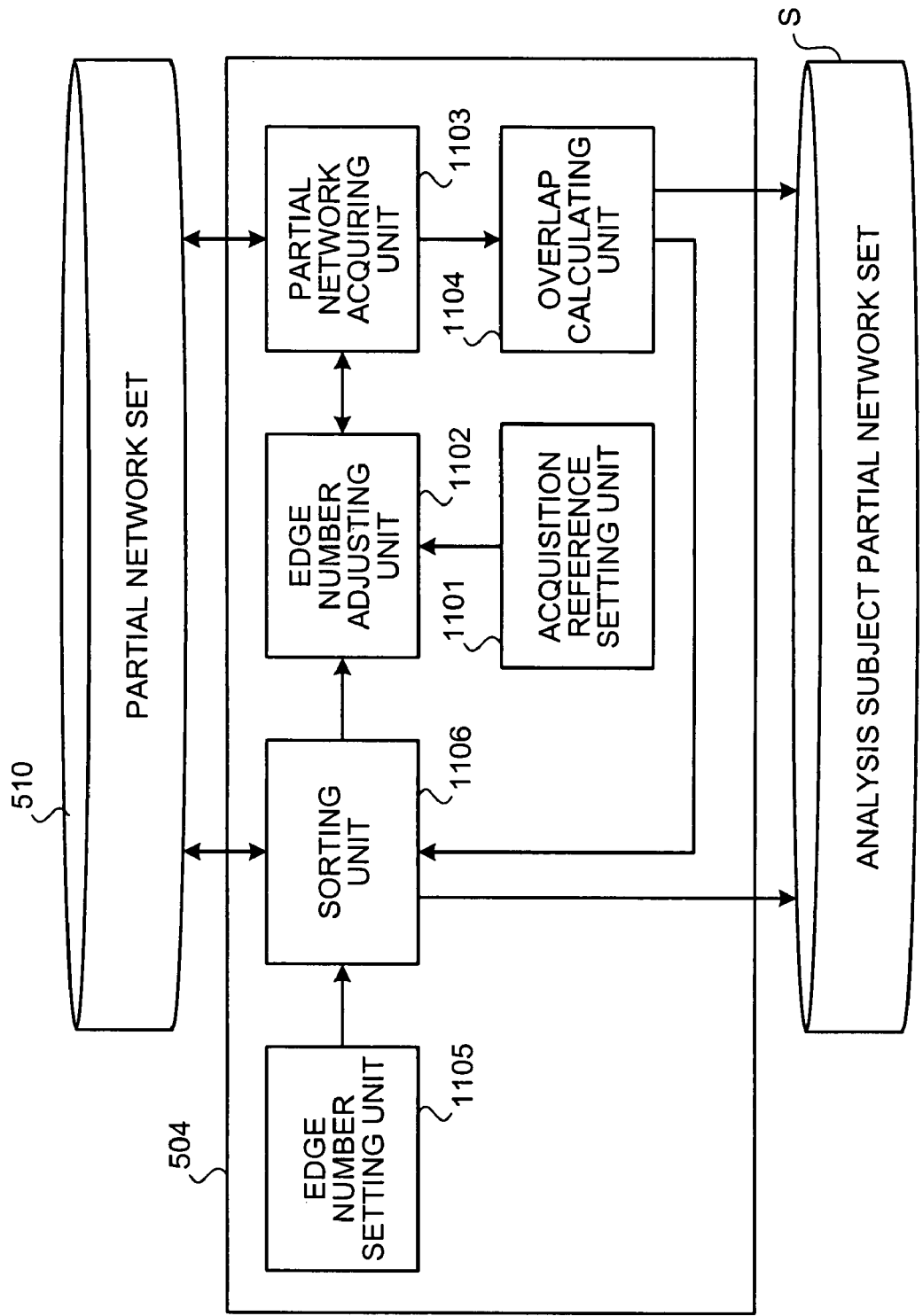
FIG. 11 a block diagram of a sort processing unit.

FIG. 11 is a block diagram of the sort processing unit 504. The sort processing unit 504 includes an acquisition reference setting unit 1101, an edge number adjusting unit 1102, a partial network acquiring unit 1103, an overlap calculating unit 1104, an edge number setting unit 1105, and a sorting unit 1106.

First, the acquisition reference setting unit 1101 sets the number of edges Ne that is an acquisition reference for acquisition of the partial network by the partial network acquiring unit 1103. An initial value of the number of edges Ne is, for example, a maximum number of edges Nmax among edge quantities in the partial network set 510.

The edge number adjusting unit 1102 adjusts the acquisition reference so that the number of edges is decreased in stages. Specifically, the number of edges Ne is decreased by a predetermined number (for example, 1). If the partial network having the number of edges Ne is not in the partial network set 510, the number of edges Ne is decreased.

The partial network acquiring unit 1103 acquires the partial network having the number of edges Ne set by the acquisition reference setting unit 1101 from the partial network set 510. If the partial network having the number of edges Ne is not in the partial network set 510, the edge number adjusting unit 1102 decreases the number of edges Ne.

The partial network acquiring unit 1103 acquires the partial network having the number of edges Ne that has been adjusted by the edge number adjusting unit 1102 from the partial network set 510. If an acquirable partial network is not in the partial network set 510, an acquisition process is completed.

The overlap calculating unit 1104 calculates a degree of overlap of the partial network having the number of edges Ne (hereinafter, "acquired partial network"), and a set of partial networks S that are selected to be the analysis subject earlier (analysis subject partial network set) with each other. Specifically, the number of edges shared between the acquired partial network and the analysis subject partial network set S (number of common edges Nc) is calculated as the overlap.

The edge number setting unit 1105 sets number of edges Ncu (Ncu≧1) as a sort reference. The number of edges Ncu is a reference for sorting the partial network set 510 by the sorting unit 1106. The number of edges Ncu is specified by the user. The number of edges Ncu is an upper limit of the number of common edges Nc that are common for the partial network and the analysis subject partial network set S. The partial network is acquired by the partial network acquiring unit 1103. The analysis subject partial network set S is sorted by the sorted unit 1106.

The sorting unit 1106 sorts partial networks in the partial network set 510 into analysis subjects and non-analysis subjects, based on the overlap. Specifically, the acquired partial networks are separated into partial networks of the analysis subject (hereinafter, "analysis subject partial network") and partial networks of the non-analysis subject (hereinafter, "non-analysis subject partial network"), based on the number of common edges Nc and the number of edges Ncu.

When the number of common edges Nc and the number of edges Ncu that is the upper limit of the number of common edges Nc are compared and it is not Nc>Ncu, the sorting unit 1106 determines an acquired partial network to be a new selected partial network. The sorting unit 1106 adds the acquired partial network to the analysis subject partial network set S. If the analysis subject partial network set S is an empty set (S=Φ), or in other words, non-analysis subject partial network is present, Nc=0. As a result, the acquired partial network is determined to the analysis subject partial network and is added to the analysis subject partial network set S.

Figure 12:
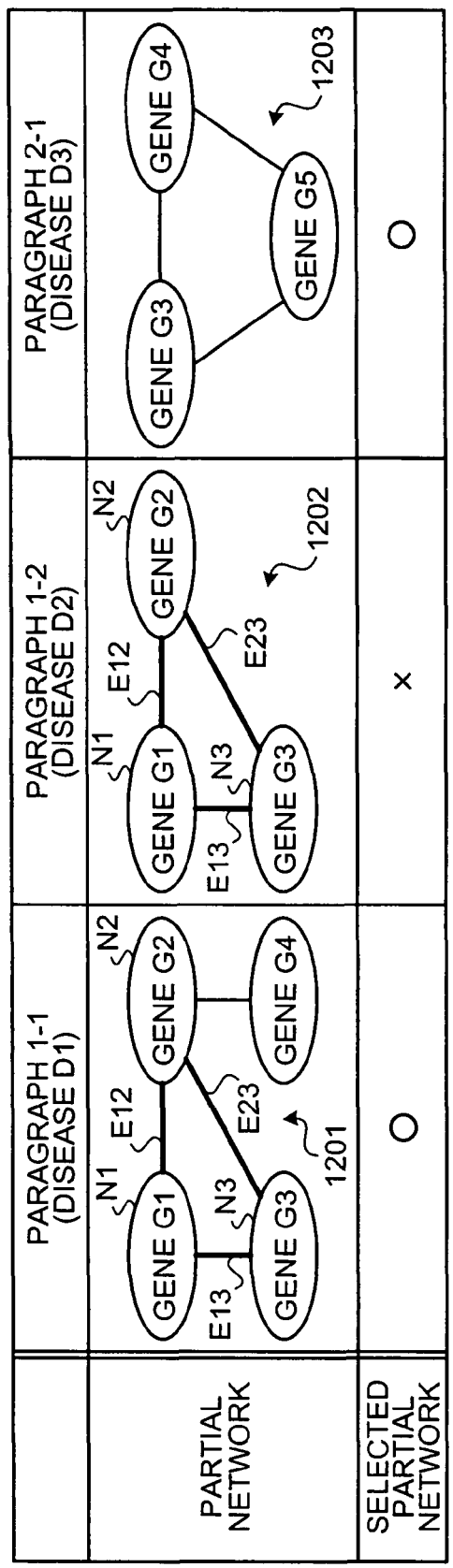
FIG. 12 is a schematic for illustrating a partial network sorting process by a sorting unit.

FIG. 12 is a schematic for illustrating a sorting process of the partial network by the sorting unit 1106. Partial networks 1201 to 1203 shown in FIG. 12 are ultimately generated by the generation processing unit 503.

A partial network 1201 is related to the paragraph 1-1 of the disease annotation 200 (disease D1). A partial network 1202 is related to the paragraph 1-2 of the disease annotation 200 (disease D2). A partial network 1203 is to the paragraph 2-1 of the disease annotation 200 (disease D3).

If the partial network 1201 is the selected partial network and the partial network 1202 is the acquired partial network, edges E12, E13, and E23 are shared edges (indicated by bold lines in FIG. 12). Therefore, number of common edges Nc of the partial networks 1201 and 1202 is three edges.

In this way, the partial networks that are ultimately in the analysis subject partial network set S are output from the output processing unit 505. In the example in FIG. 12, first, the partial network 1201 having a largest number of edges Ne (four edges) is acquired from the partial network set 510. The analysis subject partial network does not present at this point. Therefore, the partial network 1201 having the largest number of edges Ne (four edges) is determined to be the analysis subject partial network and is added to the analysis partial network set S.

The partial network 1201 having the largest number of edges Ne is unconditionally determined to be the analysis subject partial network. Therefore, the gene interactions of the partial networks having the number of edges Ne that is equal to or less than the largest number of edges Ne and equal to or higher than the number of common edges Nc shared with the partial network 1201 can be covered.

Next, the partial network acquiring unit 1103 acquires the partial network 1202 of which the number of edges Ne=3 from the partial network set 510. The number of edges Ne=3 in the partial network 1203, as well. If a plurality of partial networks has the same number of edges Ne, any one of the partial networks can be acquired.

Here, the partial network 1202 is acquired first. The overlap calculating unit 1104 calculates the number of common edges Nc that are common for the partial network 1201 within the analysis subject partial network set S. In this case, as shown in FIG. 12, the number of common edges Nc=3. If the upper limit Ncu=2, Nc>Ncu is satisfied. Therefore, the partial network 1202 is not determined to be the analysis subject partial network.

In other words, the nodes N1 to N3 and the edges E12, E13, and E23 that specify the gene interactions of the partial network 1202 are included in the partial network 1201. As a result, the partial network 1202 can be excluded from the analysis subject. Therefore, overlapping of the analysis subject partial networks that are the analysis subjects can be suppressed, and the analysis can be performed with more efficiency.

Finally, the partial network acquiring unit 1103 acquires the partial network 1203 of which the number of edges Ne=3 from the partial network set 510. The number of common edges Nc common for the partial network 1203 and the partial network 1201 is Nc=0. Therefore, the partial network 1203 is added to the analysis subject partial network set S as a new analysis subject network. The partial networks 1201 and 1203 are selected as the analysis subject partial networks.

Figure 13:
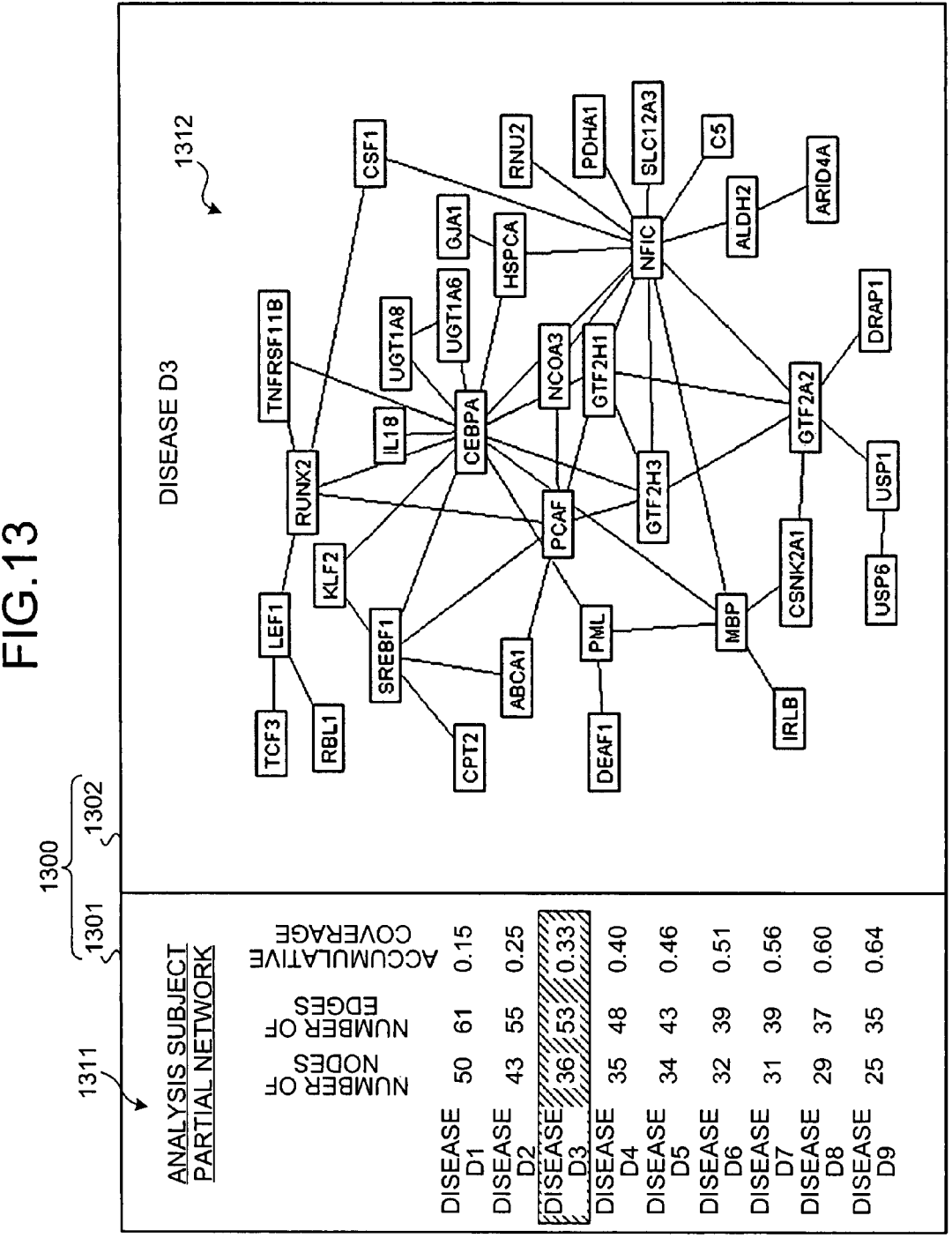
FIG. 13 is a schematic of a display example for an analysis subject partial network.
Figure 14:
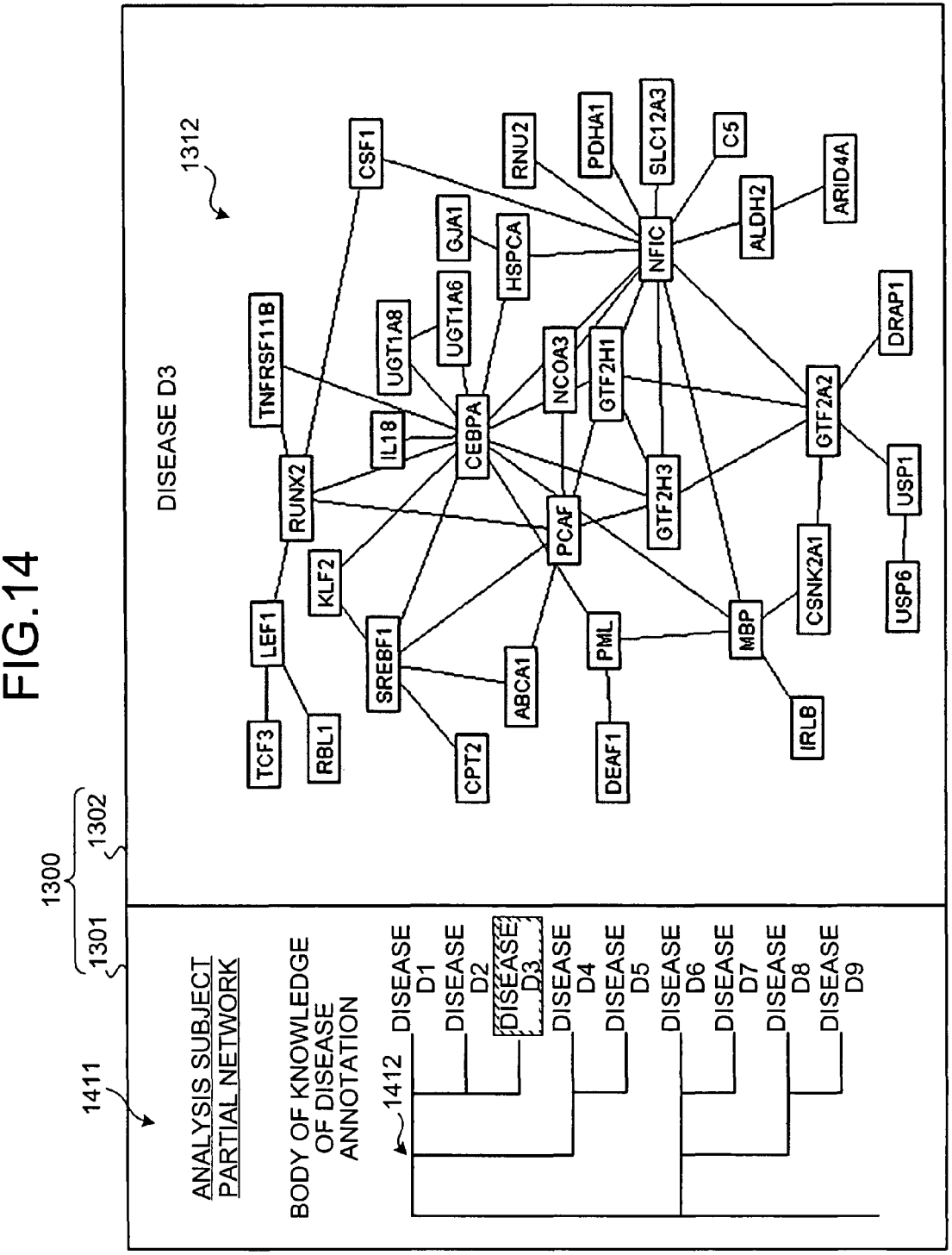
FIG. 14 is a schematic of a display example for the analysis subject partial network.

FIG. 13 and FIG. 14 are schematics of a display example of the analysis subject partial network. As shown in FIG. 13, detailed information 1311 of each analysis subject partial network is displayed on a left pane 1301 of a display screen 1300. The detailed information 1311 is, for example, a node quantity, the number of edges, and an accumulative coverage of the analysis subject partial network for each disease, D1 to D9.

Each disease, D1 to D9, can be designated by the keyboard 110 or the mouse 111, shown in FIG. 1. By viewing the detailed information 1311, the user can designate the analysis subject partial network of the disease the user wishes to analyze. When the user has designated the disease D3, for example, a network diagram 1312 indicating the partial network related to the designated disease D3 is displayed on a right pane 1302.

As shown in FIG. 14, detailed information 1411 that differs from the detailed information 1311 is displayed. A Body of Knowledge tree 1412 of the disease annotation 200 shown in FIG. 2 is displayed as the detailed information 1411. Diseases D1 to D9 are displayed at the ends of the tree 1412.

As shown in FIG. 13, each of disease D1 to D9 can be designated by the keyboard 110 or the mouse 111. By viewing the detailed information 1411, the user can designate the analysis subject partial network of the disease the user wishes to analyze. When the user has designated the disease D3, for example, the network diagram 1312 indicating the partial network related to the designated disease D3 is displayed on the right pane 1302.

Figure 15:
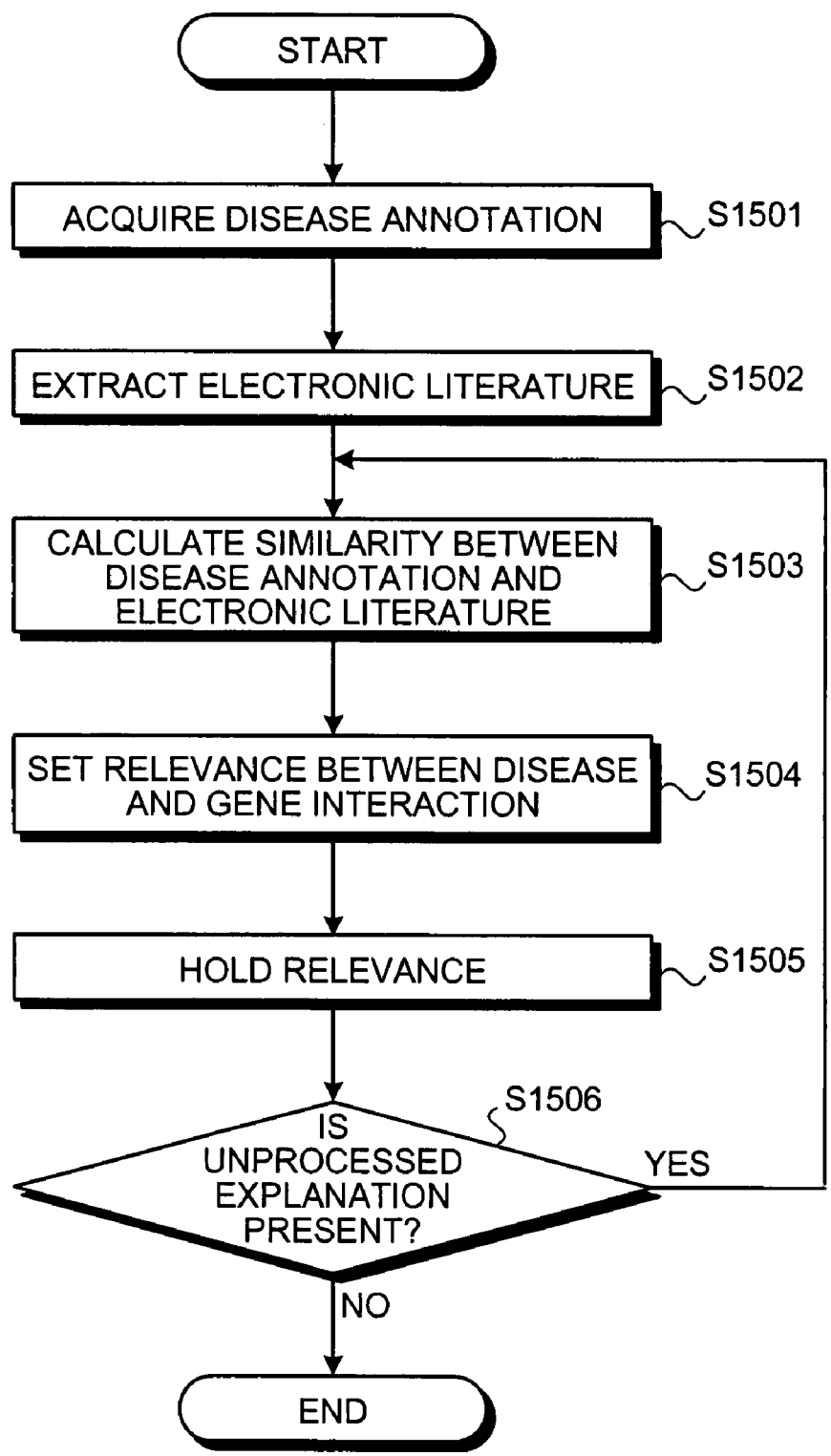
FIG. 15 is a flowchart of a relevance calculation process by a relevance calculating unit shown in FIG. 5.

FIG. 15 is a flowchart of the relevance calculating process by the relevance calculating unit 501. The disease annotation 200 shown in FIG. 2 is acquired (step S1501). Electronic literature A1 to An are extracted from the medical literature DB (step S1502). The similarity calculating unit 511 calculates the similarity between the explanation 200-$k$ in the disease annotation 200 and each electronic literature Ai (step S1503). The explanation 200-$k$ specifies the disease Dk. The relevance setting unit 512 sets the relevance Rjk between the gene interaction Ij and the disease Dk (step S1504).

The relevance DB 400 holds the set relevance Rjk (step S1505). Then, whether an unprocessed explanation is present within the disease annotation 200 is judged (step S1506). If the unprocessed explanation is present (step S1506: YES), the process returns to step S1503 and the similarity between the unprocessed explanation and each electronic literature Ai is calculated. At the same time, no unprocessed explanation is present (step S1506: NO), a series of processes is completed. As a result, the relevance DB 400 can be automatically constructed.

Figure 16:
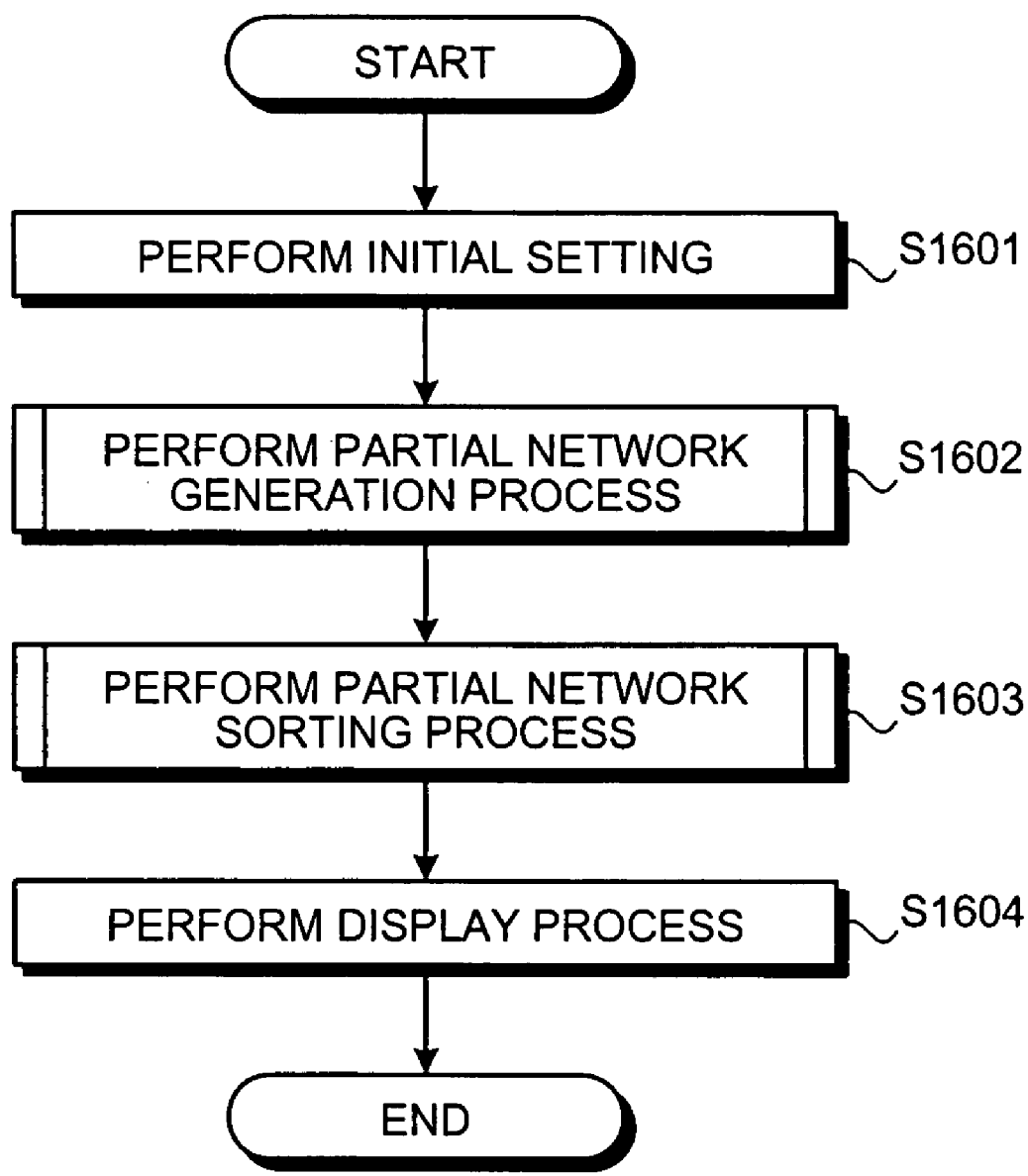
FIG. 16 is a flowchart of a process performed by the apparatus according to the embodiment.

FIG. 16 is a flowchart of a process performed by the apparatus 500. First, an initial setting is performed (step S1601). In the initial setting, the threshold T of the relevance R, the reduction amount ΔT of the relevance R, the node quantity and the number of edges of the partial network that is a composition source of a composite network (predetermined value Na), the specified coverage Ct, the upper limit Ncu of the number of common edges Nc, and the like are set. The threshold T of the relevance E is set to the upper limit of the relevance R.

Next, the generation processing unit 503 performs a partial network generation process (step S1602). The sort processing unit 504 performs a partial network sorting process (step S1603). The output processing unit 505 performs a display process of the analysis subject partial network (step S1604). As a result, the detailed information 1311 and the detailed information 1411 of the analysis subject partial network and the network diagram 1312, such as those shown in FIG. 13 and FIG. 14, can be displayed.

Figure 17:
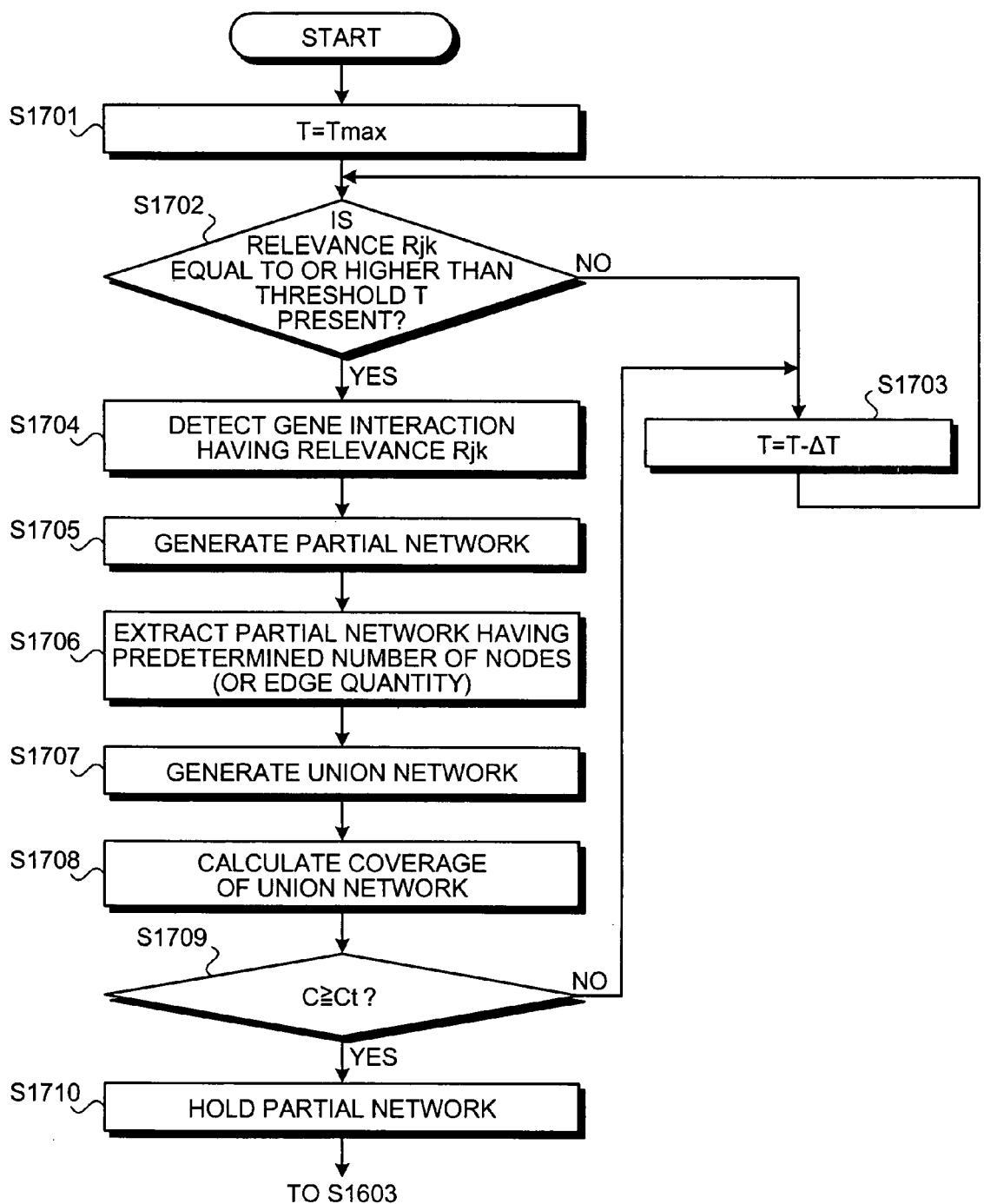
FIG. 17 is a flowchart of a partial network generation process.

FIG. 17 is a flowchart of the partial network generation process. First, the threshold T of the relevance R is set to Tmax (step S1701). The upper limit of the relevance Rjk=1, and therefore, T=1.

Next, whether the gene interaction Ij is present in the relevance DB 400 is judged (step S1702). The gene interaction Ij has the relevance Rjk with any one of the diseases Dk that is equal to or higher than the threshold T. If no gene interaction Ij is present (step S1702: NO), the threshold T is reduced by ΔT (step S1703) and the process returns to step S1702.

At the same time, if a corresponding gene interaction Ij is present in the relevance DB 400, all gene interactions Ij (combinations of genes specifying the gene interaction Ij) are detected from the relevance DB 400 (step S1704).

The gene interaction network 800 is divided for each disease and the partial networks 901 to 903 are generated (step S1705). Next, the union network generating unit 707 extracts the partial network having the number of nodes (or the number of edges) Na, from among the partial networks 901 to 903 (step S1706). Then, the union network generating unit 707 generates the union network 1000 (step S1707). The coverage calculating unit 708 calculates the coverage of the union network 1000 (step S1708).

Then, the coverage judging unit 710 judges whether C≧Ct is satisfied (step S1709). If C≧Ct is not satisfied (step S1709: NO), the process returns to step S1703. The threshold T decreases by a process loop, and the detected number of gene interactions at step S1704 increase. As a result, the union network at step S1707 can be gradually increased with the reduction amount ΔT. The coverage of the gene interaction network 800 of the partial network set 510 can be enhanced.

At the same time, if C≧Ct is satisfied (step S1709: YES), the partial networks 901 to 903 are held (step S1710). Then, the process returns to the partial network sorting process (step S1603).

Figure 18:
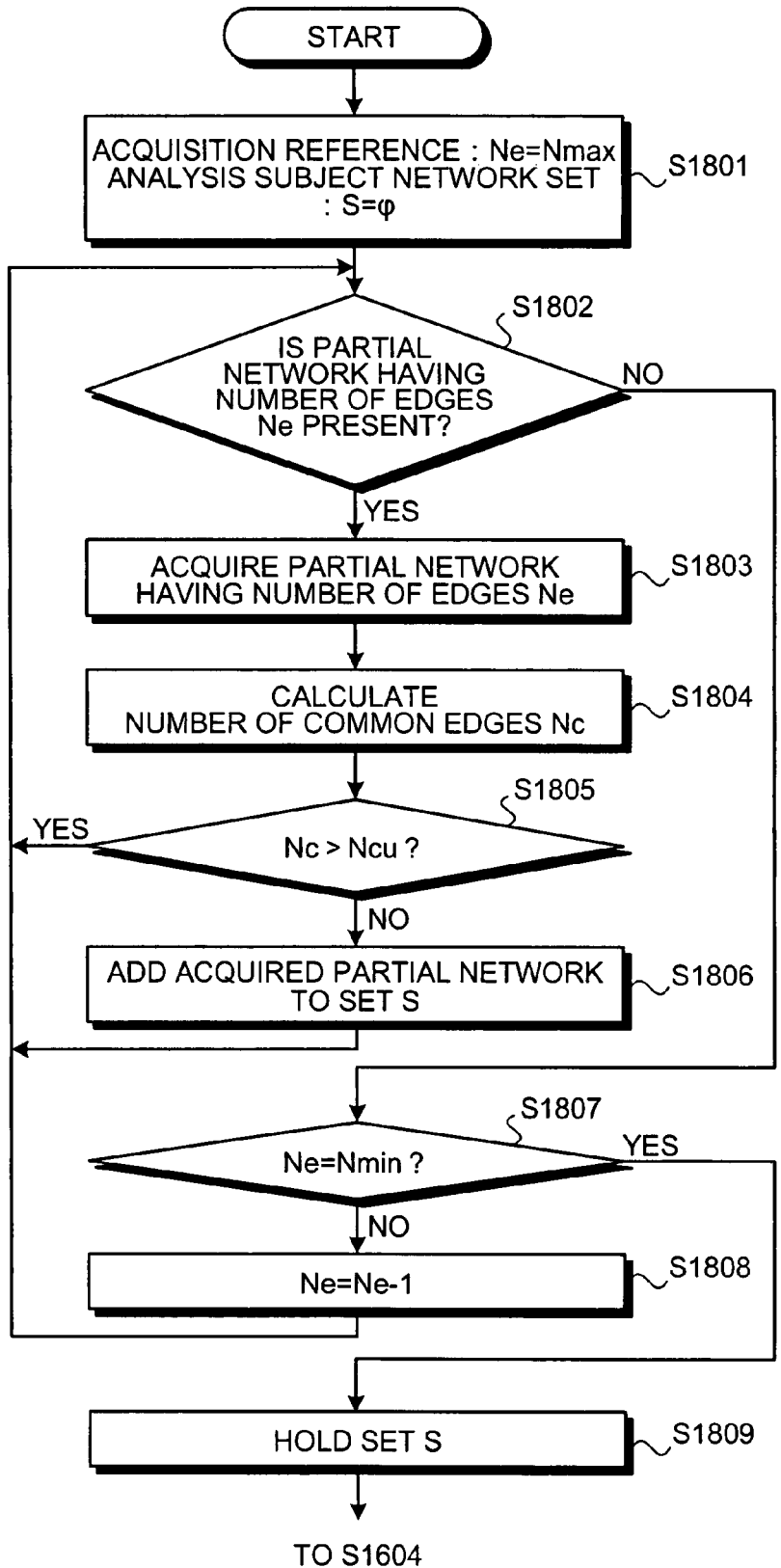
FIG. 18 is a flowchart of the partial network generation process.

FIG. 18 is a flowchart of the partial network sorting process. The acquisition reference is set to the maximum number of edges (Ne=Nmax) among the edge quantities of the partial networks in the partial network set 510. In the initial stage, the analysis subject partial network set S is the empty set (S=Φ) (step S1801).

At step S1802, the partial network acquiring unit 1103 judges whether the partial network having the number of edges Ne is in the partial network set 510. If the partial network is in the partial network set 510 (step S1802: YES), the partial network having the number of edges Ne is acquired (step S1803). Then, the overlap calculating unit 1104 calculates the number of common edges Nc common for the acquired partial network and the partial network within the analysis subject partial network set S (step S1804). In the initial stage, S=Φ, and therefore, the number of common edges Nc=0.

Then, whether Nc>Ncu is judged (step S1805). If Nc>Ncu is not satisfied (step S1805: NO), the acquired partial network is added to the analysis subject partial network set S (step S1806), and the process returns to step S1802. At the same time, if Nc>Ncu is satisfied (step S1807: YES), the process returns to step S1802 without the extracted partial network being added to the analysis subject partial network set S.

If no partial network having the number of edges Ne is present at step S1802 (step S1802: NO), whether the number of edges Ne is the minimum number of edges Nmin among the partial network set 510 is judged (step S1807).

If it is not Ne=Nmin (step S1807: NO), the number of edges Ne is decremented (step S1808), and the process returns to step S1802. At the same time, if Ne=Nmin (step S1807: YES), the analysis subject partial network set S is held (step S1809). Then, the process proceeds to the display process (step S1604).

In this way, according to the embodiment above, the gene interaction network (800 and 2100) is divided into partial networks of an appropriate size for each biological event (disease, etc.). In addition, the overall coverage of the partial networks is enhanced.

As a result, the user can select a partial network to be preferentially analyzed from relatively small number of partial networks having a size facilitating analysis, taking into consideration a relationship with a disease of interest. Therefore, with regards to a gene cluster in which changes can be seen in gene expression, a gene interaction of interest can be easily selected from a large number of possible gene interactions.

Figure 19:
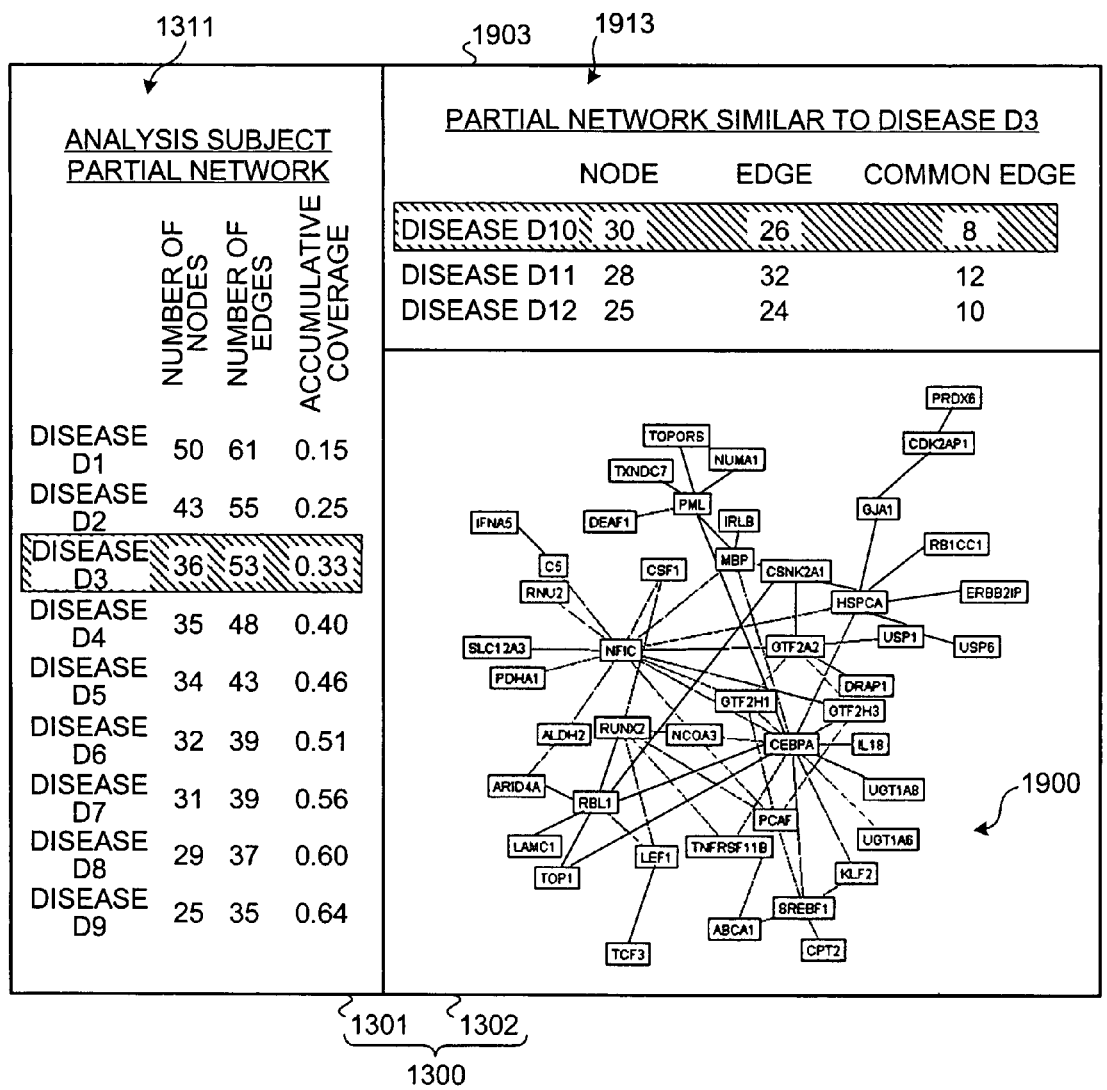
FIG. 19 is a schematic of another display example for an analysis subject partial network.

In the display process by the output processing unit 505 (step S1604), the display contents are as shown in FIG. 13 and FIG. 14. However, other forms of display are also possible. FIG. 19 is a schematic of another display example of the analysis subject partial network display. When, for example, the disease D3 is selected from the detailed information 1311 in the left pane 1301, detailed information 1913 of a partial network similar to the partial network of the disease D3 is displayed in an upper right pane 1903. Whether the partial network is similar can be judged by a common node and the number of common edges.

If, for example, a disease 10 is specified among diseases D10 to D12 in the upper right pane 1903, a network diagram 1900 of the composite network is displayed in the right pane 1302. The composite network is a composition of the partial network of the disease D3 specified in the left pane 1301 and the partial network of the disease D10 specified in the upper right pane 1903.

In the network diagram 1900 in the right pane 1302, the nodes are colored according to diseases. Common nodes are colored in an identical color. The nodes are colored in different colors when nodes on both ends of the edge specify different genes or the same gene, and when the either one of the nodes on both ends of the edge is a common node. Thus, visual understanding is facilitated in displaying the nodes.

Figure 20:
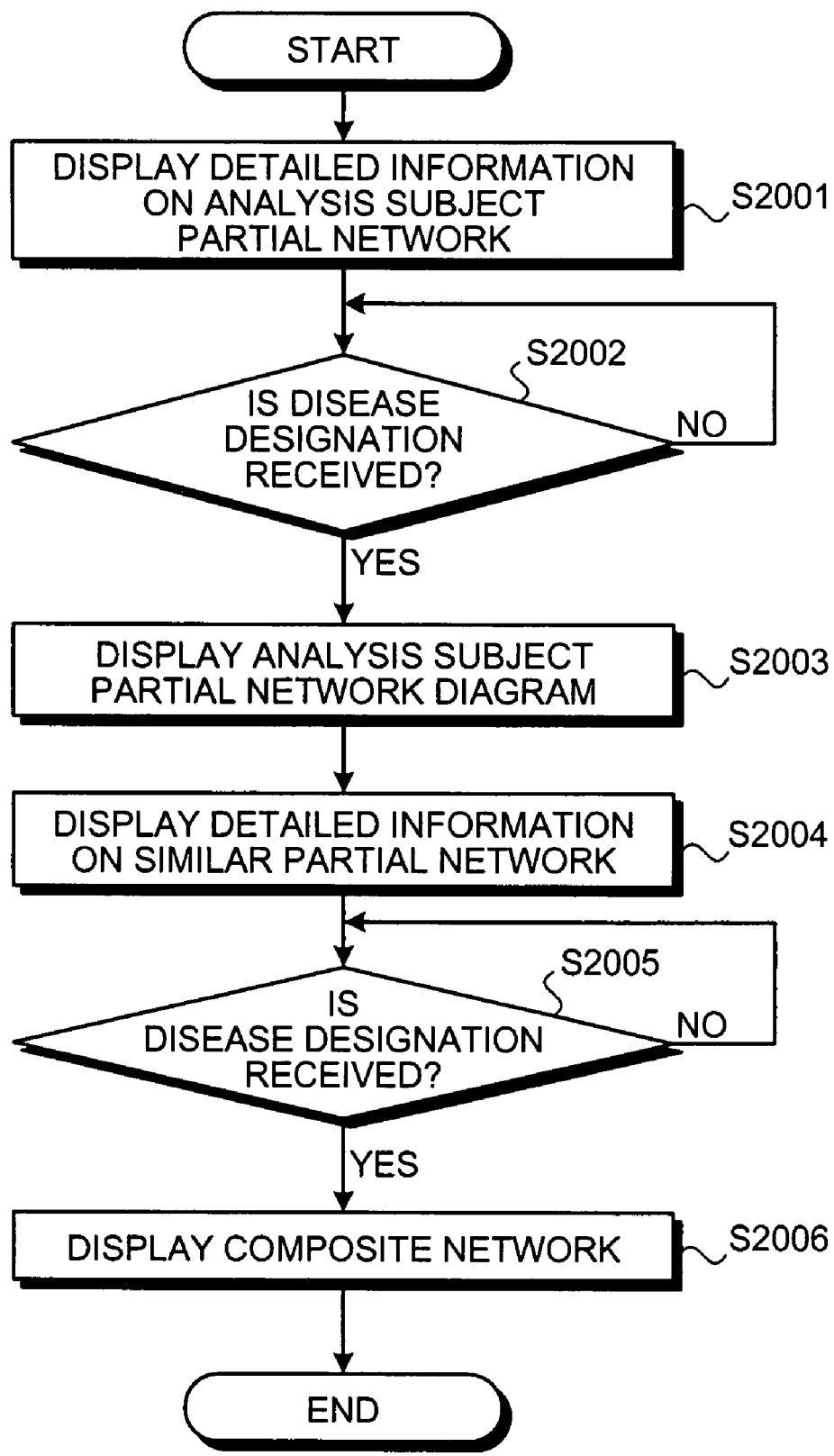
FIG. 20 is a flowchart of a display process by an output unit when the example shown in FIG. 19 is displayed.

FIG. 20 is a flowchart of a display process by the output processing unit 505 of the display example shown in FIG. 19. First, the detailed information 1311 of the analysis subject partial network is displayed (step S2001). Then, the output processing unit 505 stands by for a designation of the disease from the detailed information 1311 (step S2002: NO).

When the designation of the disease (for example, the disease D3) is received (step S2002: YES), the network diagram 1312 (see FIG. 13) of the analysis subject partial network related to the disease D3 is displayed (step S2003).

The detailed information 1913 of the partial network similar to the partial network of the specified disease D3 is also displayed (step S2004). The output processing unit 505 stands by for the designation of the disease from the detailed information 1913 (step S2005: NO). When the designation of the disease (for example, disease D10) is received (step S2005: YES), the network diagram 1900 of the composite network is displayed (step S2006). The composite network is the composition of the partial network of the disease D3 and the partial network of the disease D10. Then, the series of processes is completed.

According to the display process, the composite network indicating the gene interactions of a plurality of diseases can be displayed by the designation of a plurality of diseases that the user wishes to analyze. Therefore, a composite network having an enhanced overall coverage in an appropriately size can be provided, even when the user wishes to focus on plural diseases. Furthermore, an analysis of the gene interaction can be facilitated.

According to the embodiment, the user can select and analyze the partial networks of the gene interactions generated for each biological event. As a result, even when gene interactions caused by various biological events are present in the original gene interaction network, the user can perform the analysis efficiently by narrowing down the analysis to only the portion related to the designated biological event.

Moreover, according to the embodiment, when selecting the gene interaction based on the relevance with the biological event, the threshold of the relevance R can be automatically determined. The gene interaction having the relevance R with the biological event that is equal to or higher than the threshold can be selected. As a result, predetermined conditions for the size and the complexity of the individual partial networks to be generated and a predetermined condition for a quantity of gene interactions that should collectively be included in the generated partial networks can be met.

The condition for the size of the partial network can be a range of the number of the genes to be included in each partial network or the like. The condition for the complexity of the partial network can be a range of the number of the gene interactions to be included in each partial network (or a ratio of the number of the genes to the number of the genes interactions) or the like. The condition for the number of the gene interactions that should collectively be included in the partial networks can be a proportion (coverage) based on the gene interactions included in the original gene network or the like.

As a result, the size and the complexity of the partial network to be the candidate for the analysis subject can be controlled. Therefore, the small-scale partial network having a simple structure can be analyzed. The number of gene interactions collectively included in the output partial networks can also be controlled. Therefore, if all output partial networks are analyzed, the following user request can be met. The user requests for the guarantee that the majority of the interactions included in the original gene interaction network can be comprehensively analyzed.

Furthermore, according to the embodiment, the overlap of the gene interactions (edge overlap) is calculated between each partial network and another partial network including more gene interactions than the former partial network. If the overlap with any partial network is greater than a predetermined proportion, the partial network is eliminated from the analysis subjects. As a result, representative partial networks having a great difference from each other among the partial networks can be selected as the analysis subject partial network.

As a result, only the representative partial networks having a great difference can be handled as the analysis subject partial network. Therefore, a large number of gene interactions can be analyzed by analyzing only a relatively small number of partial networks.

Moreover, according to another aspect of the embodiment, a non-analysis subject partial network can also be output separately from the analysis subject partial networks, by correspondence with the analysis subject partial network having a high similarity with the non-analysis subject partial network (difference between included gene interactions is small).

As a result, after designating a representative analysis subject partial network having high importance, the user can analyze, in further detail, the partial networks similar to the representative analysis subject partial network, in addition to the representative analysis subject partial network. If an analysis range is widened in stages as such, the gene interactions can be comprehensively analyzed without reducing analysis efficiency. The analyzed gene interactions include the gene interactions that are overlooked when only the representative analysis subject partial network is analyzed (the gene interactions that are not included in the representative analysis subject partial network).

According to a computer program for supporting gene interaction network analysis support program, a recording medium to which the gene interaction network analysis support program is recorded, a method of supporting gene interaction analysis network, and the apparatus for supporting analysis of gene interaction network, the gene interaction network that can be easily analyzed is provided, thereby enhancing the efficiency of the analysis by the user.

The method explained in the embodiment can be actualized by an execution of a program by a computer, such as a personal computer and a work station. The program is provided in advance. The program is recorded on a recording medium that can be read by the computer, such as an HD, an FD, a CD-ROM, an MO disk, and a DVD. The program is read out from the recording medium by the computer to be executed.

According to the embodiments described above, it is possible to enhance efficiency in analysis of a gene interaction network.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A non-transitory computer-readable recording medium that stores therein a computer program for realizing a method of analyzing a gene interaction network, the computer program making a computer execute:

setting a threshold for a relevance between one of a plurality of biological events and a respective one of a plurality of gene interactions forming the gene interaction network;

detecting gene interactions from among the plurality of gene interactions having a relevance equal to or higher than the threshold;

adjusting the threshold to be low when no gene interaction is detected at the detecting;

generating partial networks for respective biological events by arranging the detected gene interactions according to the biological events;

sorting the partial networks into an analysis subject and a non-analysis subject, based on a degree of overlap of the partial networks with each other;

setting a limiting condition to limit any one of number of genes and number of gene interactions;

setting a coverage condition for a coverage of analysis subjects;

generating a union network by arranging the partial networks for each of the plurality of biological events;

calculating a coverage that indicates to what degree the union network is included in the gene interaction network;

judging whether the coverage calculated by the calculating satisfies the coverage condition, wherein, the adjusting includes adjusting the threshold to be low when the coverage calculated by the calculating does not satisfy the coverage condition;

calculating a degree of similarity in contents between a document in which one of the plurality of biological events is explained and a literature in which one of the plurality of gene interactions is indicated;

setting the relevance between the one of the plurality of biological events and the one of the plurality of gene interactions based on the degree of similarity in contents;

extracting a partial network that satisfies the limiting condition from among the partial networks generated at the generating; and displaying the partial networks on a display screen.

2. The computer-readable recording medium according to claim 1, wherein the computer program further makes the computer execute:

detecting a gene interaction having a relevance equal to or higher than the adjusted threshold from among the gene interactions, wherein the generating includes generating the partial networks by arranging the gene interactions having the relevance equal to or higher than the adjusted threshold.

3. The computer-readable recording medium according to claim 1, wherein the computer program further makes the computer execute:

setting a number of edges as an acquisition reference for acquisition of the partial network;

adjusting the acquisition reference such that the number of edges decreases in stages;

acquiring a partial network having a same number of edges as that of the acquisition reference from among the set of partial networks; and calculating a degree of overlap of the acquired partial network and a set of partial networks sorted into the analysis subject with each other, and wherein the sorting includes sorting the acquired partial network into the analysis subject and the non-analysis subject, based on the degree of overlap calculated at the calculating.

4. The computer-readable recording medium according to claim 3, wherein:

the adjusting includes adjusting the acquisition reference by decreasing the number of edges by a predetermined number when the partial network having the same number of edges as that of the acquisition reference is not present in the partial networks; and the acquiring includes acquiring a partial network having same number of edges as that of adjusted acquisition reference.

5. The computer-readable recording medium according to claim 3, wherein:

the computer program further makes the computer execute:

setting the number of edges as a sort reference for sorting the partial networks, and the sorting includes sorting the partial networks into the analysis subject and the non-analysis subject, based on the degree of overlap calculated at the calculating and the sort reference.

6. The computer-readable recording medium according to claim 1, wherein:

the displaying includes displaying, when a partial network of a biological event is designated from among the partial networks, a network that is a composite of (1) the partial network of the biological event and (2) a partial network similar to the partial network of the biological event.

7. An apparatus for supporting analysis of a gene interaction network, comprising:

a threshold setter configured to set a threshold for a relevance between one of a plurality of biological events and respective one of a plurality of gene interactions from among gene interactions forming the gene interaction network;

a relevance calculator calculating a relevance between the one of the plurality of biological events and the one of the plurality of gene interactions;

a detector configured to detect gene interactions from among the plurality of gene interactions having a relevance equal to or higher than the threshold;

a threshold adjuster configured to adjust the threshold to be low when no gene interaction is detected by the detector;

a partial network generator configured to generate partial networks for each of the plurality of biological events by arranging the detected gene interactions according to the biological event;

a sorter configured to sort the partial networks into an analysis subject and a non-analysis subject, based on a degree of overlap of the partial networks with each other;

a first condition setter configured to set a limiting condition to limit any one of a number of genes and a number of gene interactions;

a second condition setter configured to set a coverage condition for a coverage of analysis subjects;

a union network generator configured to generate a union network by arranging the partial networks for each of the plurality of biological events;

a coverage calculator configured to calculate a coverage that indicates to what degree the union network is included in the gene interaction network;

a judging unit configured to judge whether the coverage calculated by the coverage calculator satisfies the coverage condition, wherein, the threshold adjuster adjusts the threshold to be low when the coverage calculated by the coverage calculator does not satisfy the coverage condition;

a similarity calculator configured to calculate a degree of similarity in contents between a document in which one of the plurality of biological events is explained and a literature in which one of the plurality of gene interactions is indicated;

a relevance setter configured to set the relevance between one of the plurality of biological events and one of the plurality of gene interactions based on the degree of similarity in contents;

a partial network extractor configured to extract a partial network that satisfies the limiting condition from among the partial networks generated by the partial network generator; and displaying the partial networks on a display screen.

8. The apparatus according to claim 7, wherein
the detector is configured to detect a gene interaction having relevance equal to or higher than the adjusted threshold from among the plurality of gene interactions.

9. An apparatus for supporting analysis of a gene interaction network, comprising:
- a setter configured to set a threshold for relevance between one of a plurality of biological events and one of a plurality of gene interactions from among gene interactions forming the gene interaction network;
- a detector configured detect gene interactions from among the plurality of gene interactions having a relevance equal to or higher than the threshold;
- a generator configured to generate a partial network for each of the plurality of biological events by arranging the plurality of gene interactions according to the biological event;
- a relevance database storing the relevance;
- a sorter configured to sort the partial networks into an analysis subject and a non-analysis subject, based on a degree of overlap of the partial networks with each other; and
- displaying the partial networks on a display screen.

10. The apparatus according to claim 9, further comprising an adjuster configured to adjust the threshold to a lower value when no gene interaction is detected by the detector, wherein
the detector is configured to detect a gene interaction having relevance equal to or higher than the adjusted threshold from among the gene interactions.

* * * * *